(12) United States Patent
Nelson et al.

(10) Patent No.: US 6,839,596 B2
(45) Date of Patent: Jan. 4, 2005

(54) MAGNET CONTROL SYSTEM FOR BATTERY POWERED LIVING TISSUE STIMULATORS

(75) Inventors: Richard J. Nelson, Canyon Country, CA (US); Joseph H. Schulman, Santa Clarita, CA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 306 days.

(21) Appl. No.: 10/080,881

(22) Filed: Feb. 21, 2002

(65) Prior Publication Data

US 2003/0171790 A1 Sep. 11, 2003

(51) Int. Cl.[7] ................................. A61N 1/00
(52) U.S. Cl. ........................................ 607/59
(58) Field of Search ..................... 607/1–156

(56) References Cited

U.S. PATENT DOCUMENTS

| | | | |
|---|---|---|---|
| 4,124,031 A | * | 11/1978 | Mensink et al. ............... 607/31 |
| 5,292,342 A | | 3/1994 | Nelson et al. |
| 5,391,188 A | | 2/1995 | Nelson et al. |
| 5,722,998 A | * | 3/1998 | Prutchi et al. ................. 607/30 |
| 6,101,417 A | | 8/2000 | Vogel et al. |
| 6,164,284 A | | 12/2000 | Schulman et al. |
| 6,185,452 B1 | | 2/2001 | Schulman et al. |
| 6,208,894 B1 | | 3/2001 | Schulman et al. |
| 6,315,721 B2 | | 11/2001 | Schulman et al. |
| 6,580,947 B1 | * | 6/2003 | Thompson ..................... 607/30 |

* cited by examiner

*Primary Examiner*—Scott M. Getzow
(74) *Attorney, Agent, or Firm*—Lee J. Mandell

(57) ABSTRACT

A programming system for controlling and/or altering an implantable device's operation using externally applied magnetic means, e.g., a permanent magnet or the like. Typically, such devices stimulate a neural pathway or muscle and/or block pain or muscle stimulation according to programmable settings, e.g., the amplitude, duration, frequency/repetition rates, etc., of stimulation pulses applied to the neural pathways/muscles. Preferably, once programmed from an external programmer, such implantable devices can operate "independently" using the externally provided programmed information. However, external programmers may be unavailable due to cost, size, or other constraints. Accordingly, embodiments of the present invention include a magnetic sensor, preferably a magnetoresistive, Hall effect, saturated core reactors, or the like, to sense an externally provided magnetic field. By externally applying magnetic fields in sequences of controlled polarities, durations, intensities, etc., and sensing these sequences and transitions, the operation of the implantable device may be altered, i.e., programmed.

26 Claims, 15 Drawing Sheets

OPEN LOOP CONTROL/MONITOR

CLOSED LOOP CONTROL

EXEMPLARY INJURY

COORDINATED CLOSED LOOP HAND CONTROL

MAGNET CONTROL SYSTEM FOR BATTERY POWERED LIVING TISSUE STIMULATORS

FIELD OF THE INVENTION

The present invention is generally directed to implantable medical devices, e.g., battery-powered implantable medical devices, and in particular to programming systems for such devices which use magnet means, e.g., a permanent magnet, to control/alter the operation of such devices.

BACKGROUND OF THE INVENTION

The present invention relates to devices and systems of such devices for monitoring and/or affecting parameters of a patient's body for the purpose of medical diagnosis and/or treatment. More particularly, systems in accordance with the invention are characterized by a plurality of devices, preferably battery powered, configured for implanting within a patient's body, each device being configured to sense a body parameter, e.g., temperature, $O_2$ content, physical position, electrical potential, etc., and/or to affect a parameter, e.g., via nerve and/or muscle stimulation.

Commonly owned U.S. Pat. Nos. 6,164,284, 6,208,894, and 6,315,721, each entitled "System of Implantable Devices For Monitoring and/or Affecting Body Parameters" and U.S. Pat. No. 6,185,452 entitled "Battery Powered Patient Implantable Device", each incorporated herein by reference in their entirety, describe devices configured for implantation within a patient's body, i.e., beneath a patient's skin, for performing various functions including: (1) stimulation of body tissue and/or sensing of body parameters, and (2) communicating between implanted devices and devices external to a patient's body. Such implantable devices are preferably powered using rechargeable batteries and are programmed, e.g., via a programmer external to the patient's body. Once programmed, such devices are capable of operating "independently" according to their programmed parameters. However, it is not always convenient to use an external programmer due to cost, size, or availability constraints. Accordingly, the present invention addresses this need by providing a programming system that can use a readily available, low cost, magnetic means or variations thereof, to program such implantable devices.

SUMMARY OF THE INVENTION

The present invention is directed to a programming system for controlling and/or altering the operation of an implantable device using magnetic means, e.g., a permanent magnet or the like, that is applied external to a patient's body. In an exemplary embodiment of the present invention, each implanted device is configured similarly to the devices described in the commonly owned U.S. Pat. No. 6,164,284 and typically comprises a sealed housing suitable for injection into the patient's body. Each housing preferably contains a power source having a capacity of at least 1 microwatt-hour and power consuming circuitry preferably including a data signal transmitter and receiver and sensor/stimulator circuitry for driving an input/output transducer. Wireless communication between a system control unit (SCU) and the other implanted devices can be implemented in various ways, e.g., via a modulated sound signal, an AC magnetic field, an RF signal, a propagated electromagnetic wave, a light signal, or electrical conduction. In a typical application, such devices are used to stimulate a neural pathway or muscle and/or block a neural pathway to alleviate pain or block stimulation of a muscle. The ability of such stimulation devices to accomplish these tasks is subject to various programmable settings, e.g., the amplitude, duration, frequency/repetition rates, etc., of stimulation pulses that are applied to the neural pathways/muscles.

Preferably, once programmed from a device external to the patient's body, e.g., an external programmer, such implantable devices can operate "independently" using the externally provided programmed information and under control of the device's internal electronics and power source. However, program changes may be desired and external programmers may be unavailable due to cost, size, or other constraints. Accordingly, embodiments of the present invention include a magnetic sensor, preferably a magnetoresistive sensor, Hall effect sensor, saturated core reactors, or the like, which can be used to sense application of an externally provided magnetic field. By externally applying magnetic fields in sequences of controlled polarities, durations, intensities, etc., and sensing these sequences and transitions using a sensor and circuitry within the implantable device, the operation of the implantable device may be altered, i.e., programmed.

A preferred system for programming one or more parameters in an implantable device, wherein said implantable device is configured for modifying and/or sensing a patient's body parameter, comprises: (1) a sensor within said implantable device sensitive to the presence of an externally applied magnetic field, (2) a controller within the implantable device coupled to the sensor for monitoring the presence of the externally applied magnetic field and determining a timing sequence for the application and removal of the externally provided magnetic field; and wherein the controller is configured to alter at least one programmable parameter of the implantable device in response to detection of an identifiable timing sequence of the application and removal of the externally provided magnetic field.

In a further aspect of a preferred embodiment of the present invention, the sensor is a magnetoresistive sensor that is capable of measuring the intensity of an applied magnetic field and this magnetic field intensity may be used as an additional input to program the implantable device.

In a still further aspect of a preferred embodiment of the present invention, the magnetoresistive sensor is combined with a bias magnet that permits the output of the magnetoresistive sensor to be analyzed to determine the polarity of an externally applied magnetic field. Accordingly, the polarity of an externally applied magnetic field may be used as an additional input to program the implantable device.

The novel features of the invention are set forth with particularity in the appended claims. The invention will be best understood from the following description when read in conjunction with the accompanying drawings.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

The present invention is directed to a programming system for controlling and/or altering the operation of an implantable device using magnetic means, e.g., a permanent magnet or the like, that is applied external to a patient's body. In an exemplary embodiment of the present invention, each implantable device is configured similarly to the devices described in the commonly owned U.S. Pat. No. 6,164,284 (hereinafter referred to as the '284 patent), and typically comprises a sealed housing suitable for injection into the patient's body. Each housing preferably contains a power source having a capacity of at least 1 microwatt-hour and power consuming circuitry preferably including a data signal transmitter and receiver and sensor/stimulator circuitry for driving an input/output transducer. In a typical application, such devices are used to stimulate a neural pathway or muscle and/or block a neural pathway to alleviate pain or block stimulation of a muscle. The ability of such stimulation devices to accomplish these tasks is subject to various programmable settings, e.g., the amplitude, duration, frequency/repetition rates, etc., of stimulation pulses that are applied to the neural pathways/muscles. An exemplary system, suitable for use with the present invention may comprise a system control unit (SCU) and one or more devices implanted in a patient's body, i.e., within the envelope defined by the patient's skin. Each such implantable device is configured to be monitored and/or controlled by the SCU via a wireless communication channel. Wireless communication between such implanted devices can be implemented in various ways, e.g., via a modulated sound signal, an AC magnetic field, an RF signal, a propagated electromagnetic wave, a light signal, or electrical conduction.

In an exemplary system, the SCU comprises a programmable unit capable of (1) transmitting commands to at least some of a plurality of implantable devices and (2) receiving data signals from at least some of those implantable devices. In accordance with a preferred embodiment, the system operates, at least in part, in closed loop fashion whereby the commands transmitted by the SCU are dependent, in part, on the content of the data signals received by the SCU.

Figure 1:
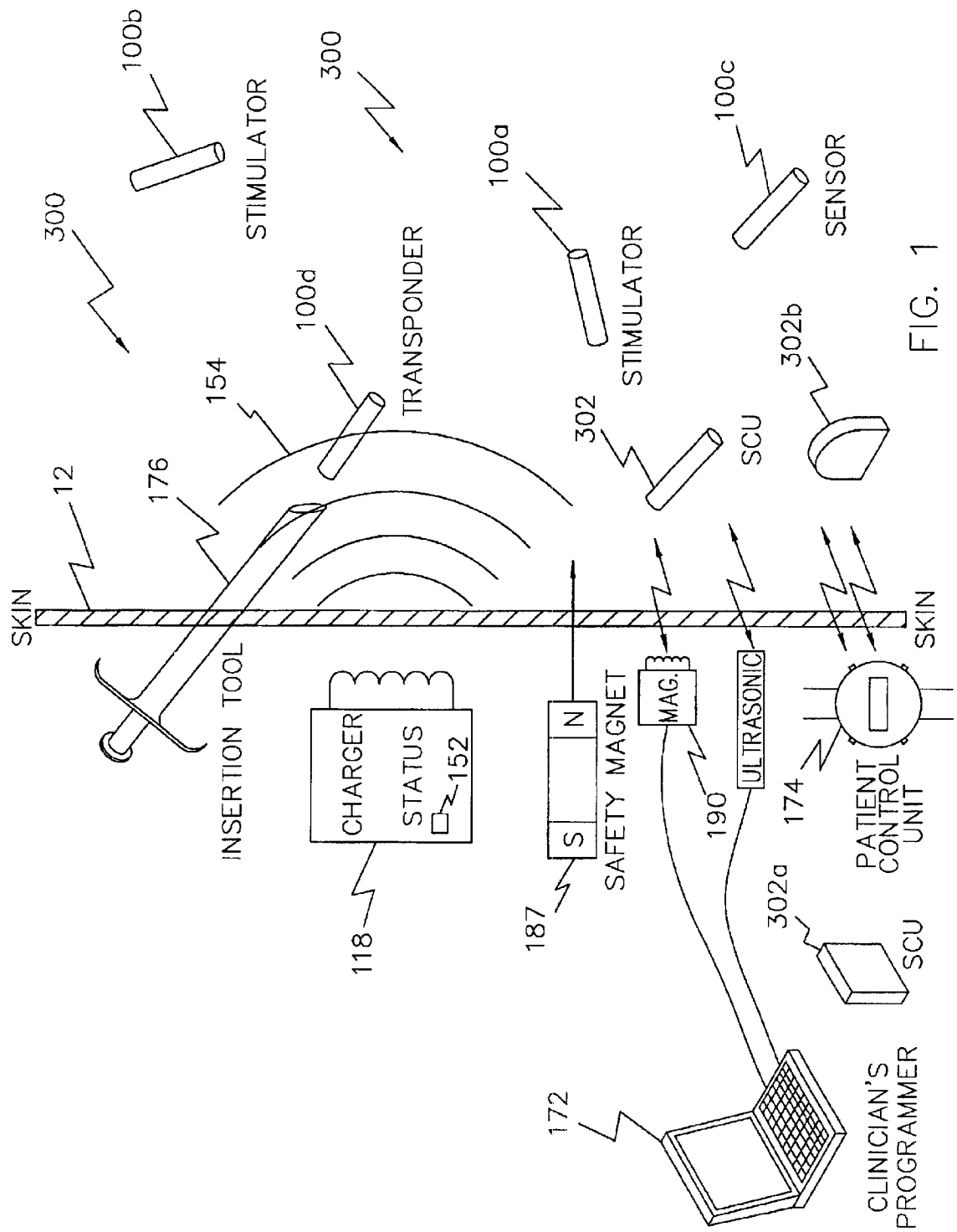
FIG. 1 is a simplified block diagram of an exemplary system suitable for practicing the present invention, the system being comprised of implanted devices, e.g., microstimulators, microsensors and microtransponders, under control of an implanted system control unit (SCU).
Figure 2:
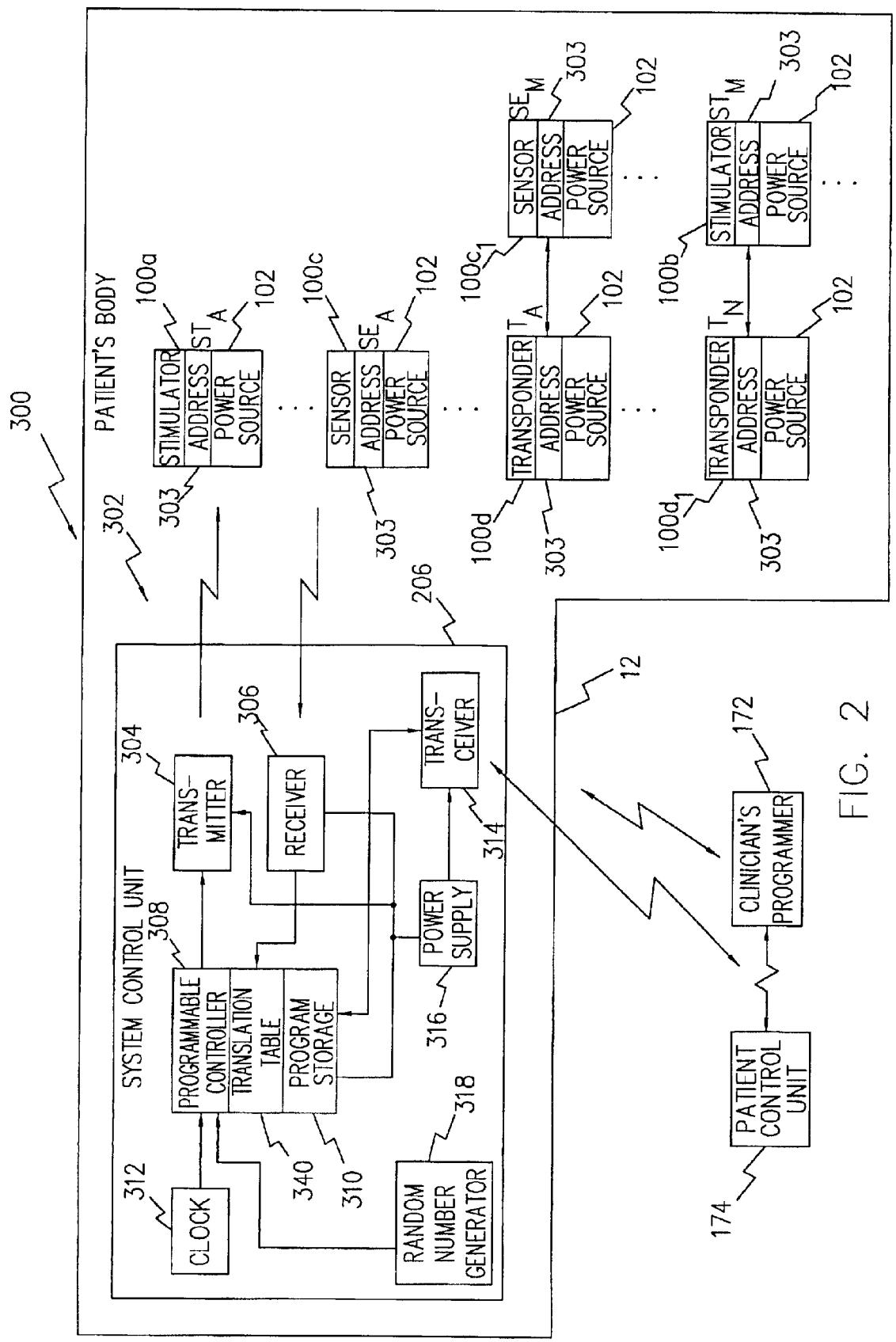
FIG. 2 comprises a block diagram of the system of FIG. 1 showing the functional elements that form the system control unit and implanted microstimulators, microsensors and microtransponders.

FIGS. 1 and 2 show an exemplary system 300 made of implanted devices 100, preferably battery powered, under control of a system control unit (SCU) 302, preferably also implanted beneath a patient's skin 12. As described in the '284 patent, potential implanted devices 100(see also the block diagram shown in FIG. 3A) include stimulators, e.g., 100*a* and 100*b*, sensors, e.g., 100*c*, and transponders, e.g., 100*d*. The stimulators, e.g., 100*a*, can be remotely programmed to output a sequence of drive pulses to body tissue proximate to its implanted location via attached electrodes. The sensors, e.g., 100*c*, can be remotely programmed to sense one or more physiological or biological parameters in the implanted environment of the device, e.g., temperature, glucose level, $O_2$ content, nerve potential, muscle potential, etc. Transponders, e.g., 100*d*, are devices which can be used to extend the interbody communication range between stimulators and sensors and other devices, e.g., a clinician's programmer 172 and the patient control unit 174. Preferably, these stimulators, sensors and transponders are contained in sealed elongate housings having an axial dimension of less than 60 mm and a lateral dimension of less than 6 mm. Accordingly, such stimulators, sensors and transponders are respectively referred to as microstimulators, microsensors, and microtransponders or referred to in general as battery-powered, implantable stimulator/sensor devices. Such microstimulators and microsensors can thus be positioned beneath the skin 12 within a patient's body using a hypodermic type insertion tool 176.

As described in the '284 patent, microstimulators and microsensors are remotely programmed and interrogated via a wireless communication channel, e.g., modulated AC magnetic, sound (i.e., ultrasonic), RF or electric fields, typically originating from control devices external to the patient's body, e.g., the clinician's programmer 172 or patient control unit 174. Typically, the clinician's programmer 172 is used to program a single continuous or one time pulse sequence into each microstimulator and/or measure a biological parameter from one or more microsensors. Similarly, the patient control unit 174 typically communicates with the implanted devices 100, e.g., microsensors 100c, to monitor biological parameters. In order to distinguish each implanted device over the communication channel, each implanted device is manufactured with an address or identification code (ID) 303 specified in address storage circuitry 108 (see FIG. 3A) as described in the '284 patent.

By using one or more such implantable devices in conjunction with the SCU 302 of the present invention, the capabilities of such implanted devices can be further expanded. For example, in an open loop mode (described below in reference to FIG. 4), the SCU 302 can be programmed to periodically initiate tasks, e.g., perform real time tasking, such as transmitting commands to microstimulators according to a prescribed treatment regimen or periodically monitor biological parameters to determine a patient's status or the effectiveness of a treatment regimen. Alternatively, in a closed loop mode (described below in reference to FIGS. 5–7), the SCU 302 periodically interrogates one or more microsensors and accordingly adjusts the commands transmitted to one or more microstimulators.

FIG. 2 shows a system 300 comprised of (1) one or more implantable devices 100 operable to sense and/or stimulate a patient's body parameter in accordance with one or more controllable operating parameters and (2) the SCU 302. The SCU 302 is primarily comprised of (1) a housing 206, preferably sealed and configured for implantation beneath the skin of the patient's body as described in the '284 patent in reference to the implanted devices 100, (2) a signal transmitter 304 in the housing 206 for transmitting command signals, (3) a signal receiver 306 in the housing 206 for receiving status signals, and (4) a programmable controller 308, e.g., a microcontroller or state machine, in the housing 206 responsive to received status signals for producing command signals for transmission by the signal transmitter 304 to other implantable devices 100. The sequence of operations of the programmable controller 308 is determined by an instruction list, i.e., a program, stored in program storage 310, coupled to the programmable controller 308. While the program storage 310 can be a nonvolatile memory device, e.g., ROM, manufactured with a program corresponding to a prescribed treatment regimen, it is preferable that at least a portion of the program storage 310 be an alterable form of memory, e.g., RAM, EEPROM, etc., whose contents can be remotely altered as described further below. However, it is additionally preferable that a portion of the program storage 310 be nonvolatile so that a default program is always present. The rate at which the program contained within the program storage 310 is executed is determined by clock/oscillator 312. Additionally, a real time clock operating in response to clock/oscillator 312 preferably permits tasks to be scheduled at specified times of day.

The signal transmitter 304 and signal receiver 306 preferably communicate with implanted devices 100 using an RF signal, e.g., a propagated electromagnetic wave, modulated by a command data signal. Alternatively, an audio transducer may be used to generate mechanical vibrations having a carrier frequency modulated by a command data signal. In an exemplary embodiment, a carrier frequency of 100 kHz is used which corresponds to a frequency that freely passes through a typical body's fluids and tissues. However, such sound means that operate at any frequency, e.g., greater than 1 Hz, are also considered to be within the scope of the present invention. Alternatively, the signal transmitter 304 and signal receiver 306 can communicate using modulated AC, e.g., magnetic fields.

The clinician's programmer 172 and/or the patient control unit 174 and/or other external control devices can also communicate with the implanted devices 100, as described in the '284 patent, preferably using a modulated RF or AC magnetic field. Alternatively, such external devices can communicate with the SCU 302 via a transceiver 314 coupled to the programmable controller 308. Since, the signal transmitter 304 and signal receiver 306 may operate using a different communication means, a separate transceiver 314 which operates using an alternative communication means may be used for communicating with external devices. However, a single transmitter 304/receiver 306 can be used in place of transceiver 314 for communicating with the external devices and implanted devices if a common communication means is used.

Figure 3A:
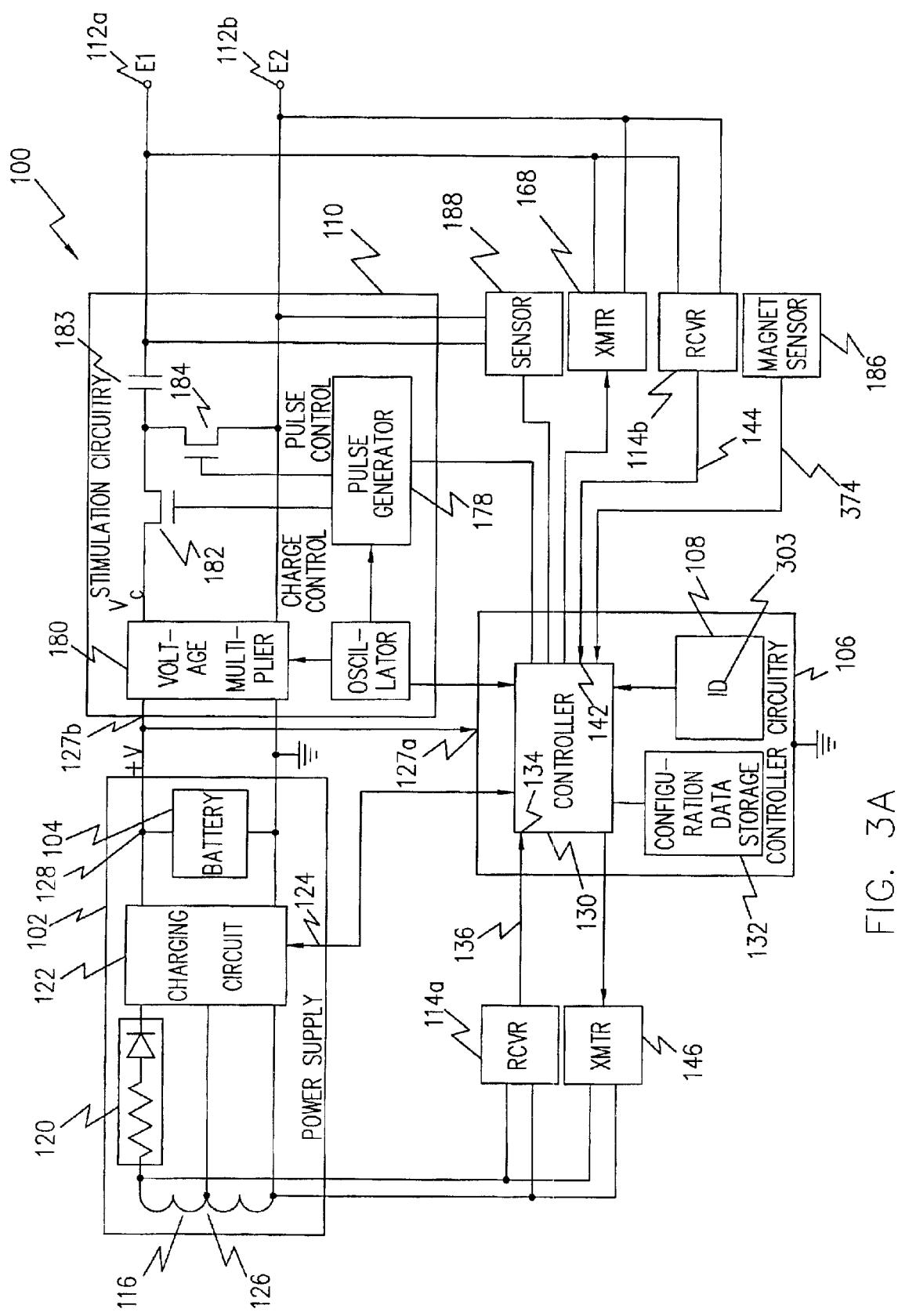
FIG. 3A comprises a block diagram of an exemplary implantable device, as shown in U.S. Pat. No. 6,164,284, including a battery for powering the device for a period of time in excess of one hour in response to a command from the system control unit.
Figure 3B:
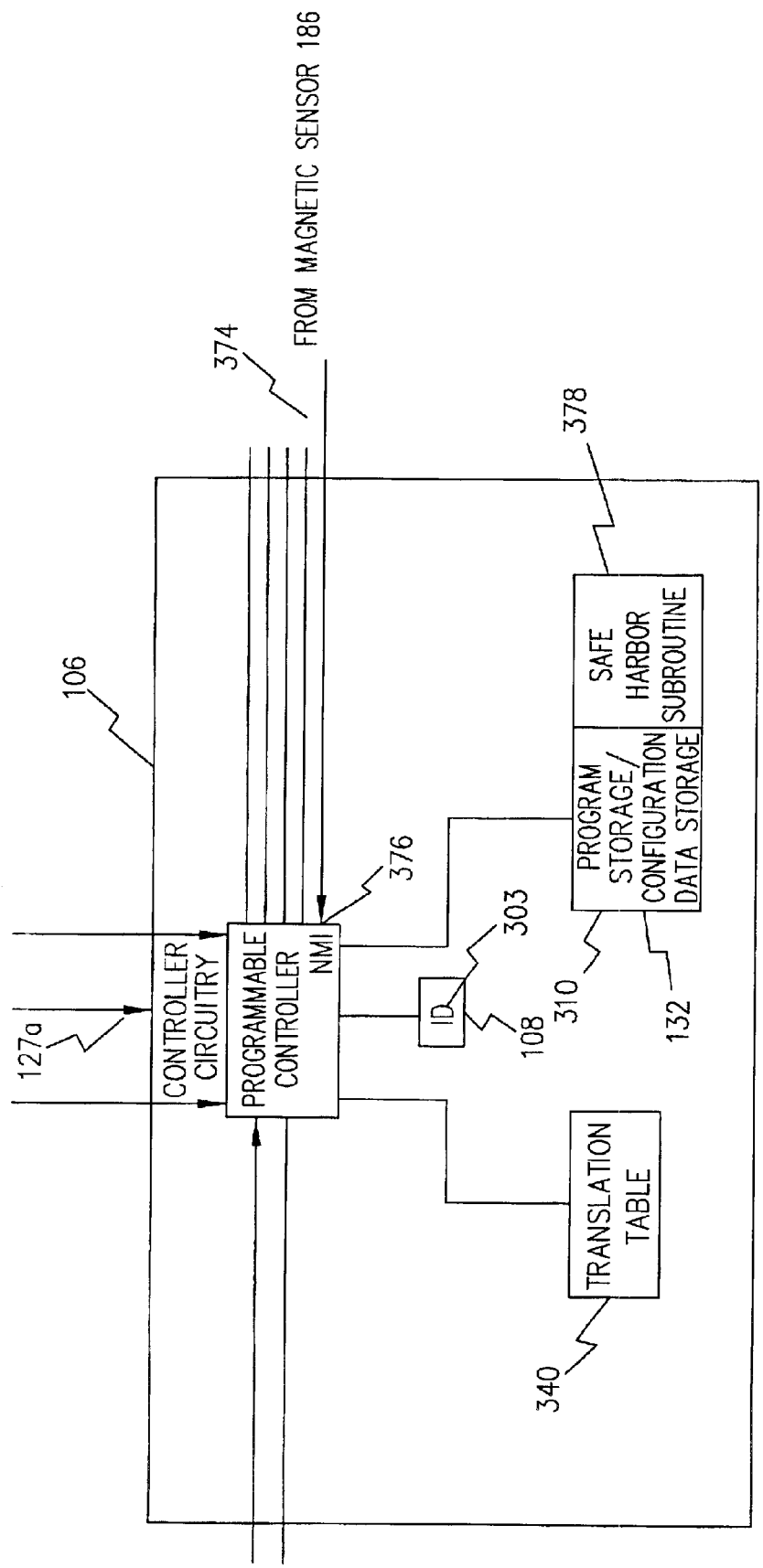
FIG. 3B comprises a simplified block diagram of controller circuitry that can be substituted for the controller circuitry of FIG. 3A, thus permitting a single device to be configured as a system control unit and/or a microstimulator and/or a microsensor and/or a microtransponder.

FIG. 3A comprises a block diagram of an exemplary implantable device 100 operable under control of controller circuitry 106 and includes a battery 104, preferably rechargeable, for powering the device for a period of time in excess of one hour and responsive to command signals from a remote device, e.g., the SCU 302. The controller circuitry 106 is primarily comprised of a controller 130, configuration data storage 132 for prescribing its operation, and address storage circuitry 108 for storing the ID 303 of the device. As described in the '284 patent, the implantable device 100 is preferably configurable to alternatively operate as a microstimulator and/or microsensor and/or microtransponder due to the commonality of most of the circuitry contained within. Such circuitry may be further expanded to permit a common block of circuitry to also perform the functions required for the SCU 302. Accordingly, FIG. 3B shows an alternative implementation of the controller circuitry 106 of FIG. 3A that is suitable for implementing a microstimulator and/or a microsensor and/or a microtransponder and/or the SCU 302. In this implementation, the configuration data storage 132 can be alternatively used as the program storage 310 when the implantable device 100 is used as the SCU 302. In this implementation, XMTR 168 corresponds to the signal transmitter 304 and the RCVR 114b corresponds to the signal receiver 306 (preferably operable via electrodes 112a and 112b operating as an RF antenna) and the RCVR 114a and XMTR 146 correspond to the transceiver 314 (preferably operable via coil 116 for AC magnetic modes of communication).

In a preferred embodiment, the contents of the program storage 310, i.e., the software that controls the operation of the programmable controller 308, can be remotely downloaded, e.g., from the clinician's programmer 172 using data modulated onto an RF signal or an AC magnetic field. In this embodiment, it is preferable that the contents of the program storage 310 for each SCU 302 be protected from an inadvertent change. Accordingly, the contents of the address storage circuitry 108, i.e., the ID 303, is preferably used as a security code to confirm that the new program storage contents are destined for the SCU 302 receiving the data. This feature is significant if multiple patients could be physically located, e.g., in adjoining beds, within the communication range of the clinician's programmer 172.

In a further aspect of the present invention, it is preferable that the SCU 302 be operable for an extended period of time, e.g., in excess of one hour, from an internal power supply 316 (see FIG. 2). While a primary battery, i.e., a nonrechargeable battery, is suitable for this function, it is preferable that the power supply 316 include a rechargeable battery, e.g., battery 104 as described in the '284 patent, that can be recharged via an AC magnetic field produced external to the patient's body. Accordingly, power supply 102 of FIG. 3A is the preferred power supply 316 for the SCU 302 as well.

The battery-powered devices 100 of the '284 patent are preferably configurable to operate in a plurality of operational modes, e.g., via a communicated command signal. In a first operational mode, device 100 is remotely configured to be a microstimulator, e.g., 100a and 100b. In this embodiment (see FIG. 3A), controller 130 commands stimulation circuitry 110 to generate a sequence of drive pulses through electrodes 112 to stimulate tissue, e.g., a nerve or muscle, proximate to the implanted location of the microstimulator, e.g., 100a or 100b. In operation, a programmable pulse generator 178 and voltage multiplier 180 are programmably configured with parameters (see exemplary Table I) corresponding to a desired pulse sequence and specifying how much to multiply (or divide) the battery voltage (e.g., by summing charged capacitors or similarly charged battery portions) to generate a desired compliance voltage $V_c$. A first FET 182 is periodically energized to store charge into capacitor 183 (in a first direction at a low current flow rate through the body tissue) and a second FET 184 is periodically energized to discharge capacitor 183 in an opposing direction at a higher current flow rate which stimulates a nearby muscle or nerve. Alternatively, electrodes can be selected that will form an equivalent capacitor within the body tissue.

TABLE I

Stimulation Parameters

| | |
|---|---|
| Current: | continuous current charging of storage capacitor |
| Charging currents: | 1, 3, 10, 30, 100, 250, 500 µa |
| Current Range: | 0.8 to 40 ma in nominally 3.2% steps |
| Compliance Voltage: | selectable, 3–24 volts in 3 volt steps |
| Pulse Frequency_(PPS): | 1 to 5000 PPS in nominally 30% steps |
| Pulse Width: | 5 to 2000 µs in nominally 10% steps |
| Burst On Time (BON): | 1 ms to 24 hours in nominally 20% steps |
| Burst Off Time (BOF): | 1 ms to 24 hours in nominally 20% steps |
| Triggered Delay to BON: | either selected BOF or pulse width |
| Burst Repeat Interval: | 1 ms to 24 hours in nominally 20% steps |
| Ramp On Time: | 0.1 to 100 seconds (1, 2, 5, 10 steps) |
| Ramp Off Time: | 0.1 to 100 seconds (1, 2, 5, 10 steps) |

In a next operational mode, the battery-powered implantable device 100 can be configured to operate as a microsensor, e.g., 100c, that can sense one or more physiological or biological parameters in the implanted environment of the device. In accordance with a preferred mode of operation, the system control unit 302 periodically requests the sensed data from each microsensor 100c using its ID 303 stored in the address storage circuitry 108, and responsively sends command signals to microstimulators, e.g., 100a and 100b, adjusted accordingly to the sensed data. For example, sensor circuitry 188 can be coupled to the electrodes 112 to sense or otherwise used to measure a biological parameter, e.g., temperature, glucose level, $O_2$ content, voltage, current, impedance, etc. and provide the sensed data to the controller circuitry 106. Preferably, the sensor circuitry 188 includes a programmable bandpass filter and an analog to digital (A/D) converter that can sense and accordingly convert the voltage levels across the electrodes 112 into a digital quantity. Alternatively, the sensor circuitry 188 can include one or more sense amplifiers to determine if the measured voltage exceeds a threshold voltage value or is within a specified voltage range. Furthermore, the sensor circuitry 188 can be configurable to include integration circuitry to further process the sensed voltage. The operational mode of the voltage sensor circuitry 188 is programmable, e.g., via the device's communication interface (see exemplary Table II) or via the magnetic programmer means of the present invention.

TABLE II

Sensing Parameters

| | |
|---|---|
| Input voltage range: | 5 µv to 1 V |
| Bandpass filter rolloff: | 24 dB |
| Low frequency cutoff choices: | 3, 10, 30, 100, 300, 1000 Hz |
| High frequency cutoff choices: | 3, 10, 30, 100, 300, 1000 Hz |
| Integrator frequency choices: | 1 PPS to 100 PPS |
| Amplitude threshold for detection choices: | 4 bits of resolution |

Additionally, the sensing capabilities of a microsensor preferably include the capability to monitor the battery status via path 124 from the charging circuit 122 and can additionally include using an ultrasonic transducer (not shown) or the coil 116 to respectively measure the ultrasonic, magnetic or propagated RF signal magnitudes (or communication time delays) of signals transmitted between a pair of implanted devices and thus determine the relative locations of these devices. This information can be used to determine the amount of body movement, e.g., the amount that an elbow or finger is bent, and thus form a portion of a closed loop motion control system.

In another operational mode, the battery-powered implantable device 100 can be configured to operate as a microtransponder, e.g., 100d. In this operational mode, the microtransponder receives (via the aforementioned RCVR 114a using AC magnetic, sonic, RF, or electric communication modes) a first command signal from the SCU 302 and retransmits this signal (preferably after reformatting) to other implanted devices (e.g., microstimulators, microsensors, and/or microtransponders) using the aforementioned XMTR 168 using magnetic, sonic, RF or electric communication modes. While a microtransponder may receive one mode of command signal, e.g., magnetic, it may retransmit the signal in another mode, e.g., RF. For example, clinician's programmer 172 may emit a modulated magnetic signal using a magnetic emitter 190 (see FIG. 1) to program/command the implanted devices 100. However, the magnitude of the emitted signal may not be sufficient to be successfully received by all of the implanted devices 100. As such, a microtransponder 100d may receive the modulated magnetic signal and retransmit it (preferably after reformatting) as a modulated ultrasonic or RF signal which can pass through the body with fewer restrictions. In another exemplary use, the patient control unit 174 may need to monitor a microsensor 100c in a patient's foot. Despite the efficiency of ultrasonic, magnetic and propagated RF communication in a patient's body, such a signal could still be insufficient to pass from a patient's foot to a patient's wrist (the typical location of the patient control unit 174). As such, a microtransponder 100d could be implanted (if needed) in the patient's torso to improve the communication link.

Figure 4:
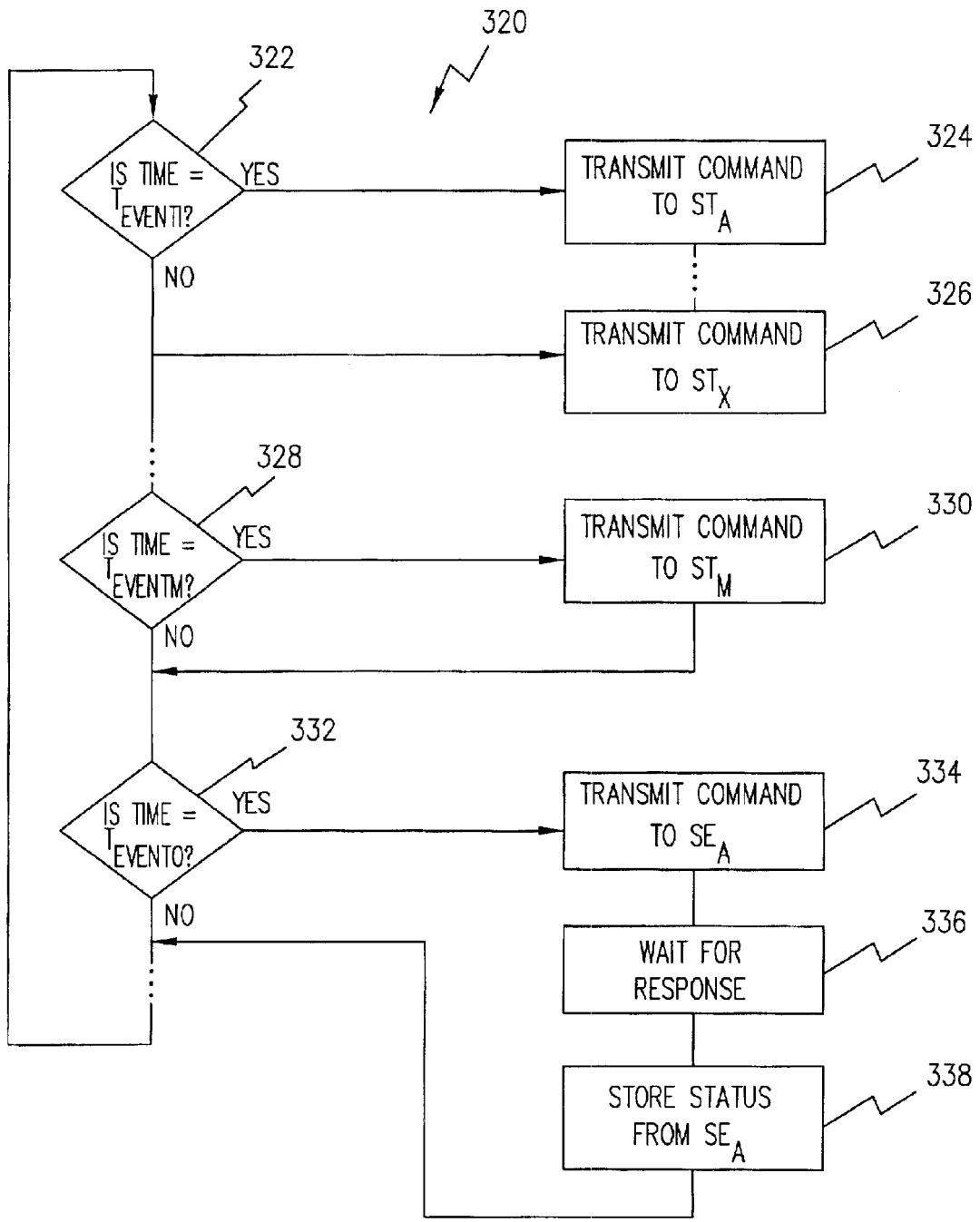
FIG. 4 shows an exemplary flow chart of the use of the exemplary system in an open loop mode for controlling/monitoring a plurality of implanted devices, e.g., microstimulators, microsensors.

FIG. 4 shows a block diagram of an exemplary open loop control program, i.e., a task scheduler 320, for controlling/monitoring a body function/parameter. In this process, the programmable controller 308 is responsive to the clock 312 (preferably a crystal controlled oscillator to thus permit real time scheduling) in determining when to perform any of a plurality of tasks. In this exemplary flow chart, the programmable controller 308 first determines in block 322 if it is now at a time designated as $T_{EVENT1}$ (or at least within a sampling error of that time), e.g., at 1:00 AM. If so, the programmable controller 308 transmits a designated command to microstimulator A ($ST_A$) in block 324. In this example, the control program continues where commands are sent to a plurality of stimulators and concludes in block 326 where a designated command is sent to microstimulator X ($ST_X$). Such a subprocess, e.g., a subroutine, is typically used when multiple portions of body tissue require stimulation, e.g., stimulating a plurality of muscle groups in a paralyzed limb to avoid atrophy. The task scheduler 320 continues through multiple time event detection blocks until in block 328 it determines whether the time $T_{EVENTM}$ has arrived. If so, the process continues at block 330 where, in this case, a single command is sent to microstimulator M ($ST_M$). Similarly, in block 332 the task scheduler 320 determines when it is the scheduled time, i.e., $T_{EVENTO}$, to execute a status request from microsensor A ($SE_A$). If so, a subprocess, e.g., a subroutine, commences at block 334 where a command is sent to microsensor A ($SE_A$) to request sensor data and/or specify sensing criteria. Microsensor A ($SE_A$) does not instantaneously respond. Accordingly, the programmable controller 308 waits for a response in block 336. In block 338, the returned sensor status data from microsensor A ($SE_A$) is stored in a portion of the memory, e.g., a volatile portion of the program storage 310, of the programmable controller 308. The task scheduler 320 can be a programmed sequence, i.e., defined in software stored in the program storage 310, or, alternatively, a predefined function controlled by a table of parameters similarly stored in the program storage 310. A similar process may be used where the SCU 302 periodically interrogates each implantable device 100 to determine its battery status.

Figure 5:
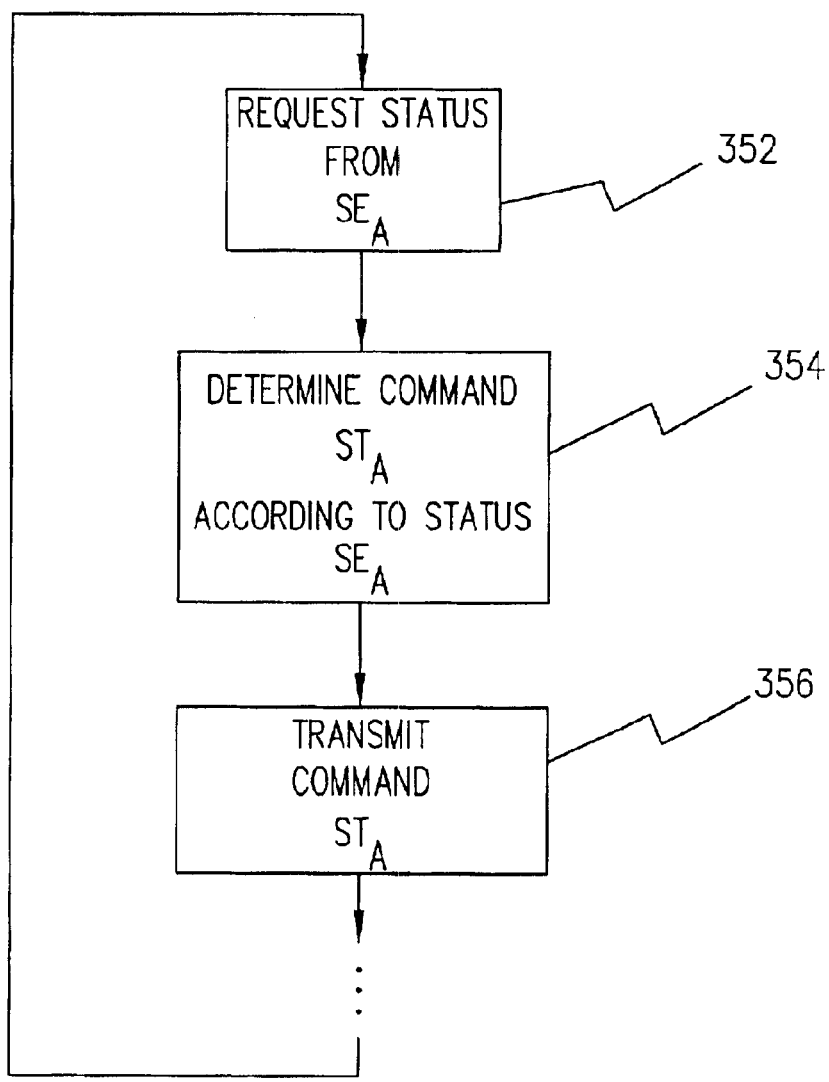
FIG. 5 shows a simplified flow chart of the use of closed loop control of a microstimulator by altering commands from the system control unit in response to status data received from a microsensor.

FIG. 5 is an exemplary block diagram showing the use of the system of the present invention to perform closed loop control of a body function. In block 352, the SCU 302 requests status from microsensor A ($SE_A$). The SCU 302, in block 354, then determines whether the present command given to a microstimulator is satisfactory and, if necessary, determines a new command and transmits the new command to the microstimulator A ($ST_A$) in block 356. For example, if microsensor A ($SE_A$) is reading a voltage corresponding to the degree of contraction resulting from stimulating a muscle, the SCU 302 could transmit a command to microstimulator A ($ST_A$) to adjust the sequence of drive pulses, e.g., in magnitude, duty cycle, etc., and accordingly change the voltage sensed by microsensor A ($SE_A$). Accordingly, closed loop, i.e., feedback, control is accomplished. The characteristics of the feedback (position, integral, derivative (PID)) control are preferably program controlled by the SCU 302 according to the control program contained in program storage 310.

Figure 6:
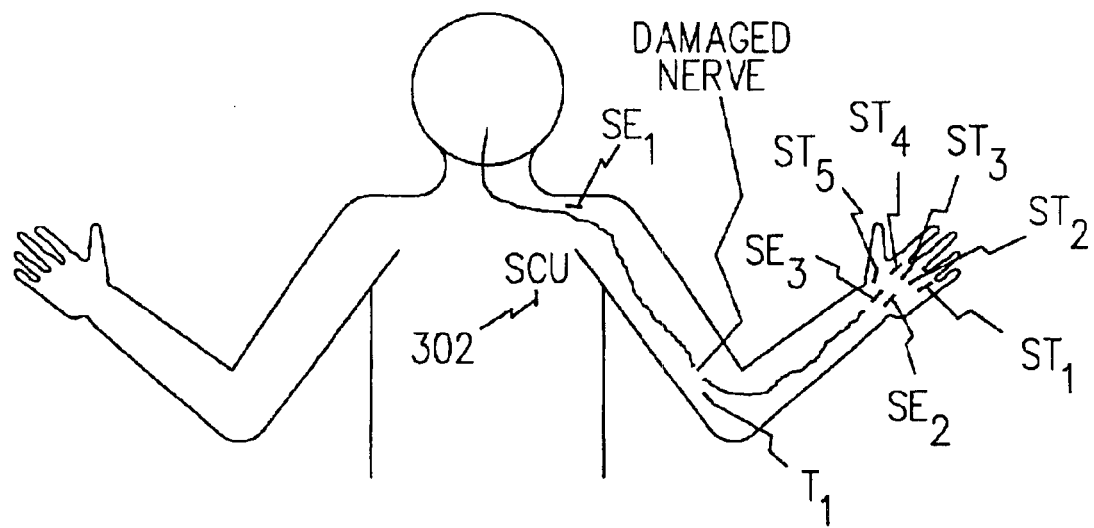
FIG. 6 shows an exemplary injury, i.e., a damaged nerve, and the placement of a plurality of implanted devices, i.e., microstimulators, microsensors and a microtransponder under control of the system control unit for "replacing" the damaged nerve.

FIG. 6 shows an exemplary injury treatable by embodiments of the present exemplary system 300. In this exemplary injury, the neural pathway has been damaged, e.g., severed, just above a patient's left elbow. The goal of this exemplary system is to bypass the damaged neural pathway to permit the patient to regain control of their left hand. An SCU 302 is implanted within the patient's torso to control a plurality of stimulators, $ST_1$–$ST_5$, implanted proximate to the muscles respectively controlling the patient's thumb and fingers (shown in the patient's hand for simplicity). Additionally, microsensor 1 ($SE_1$) is implanted proximate to an undamaged nerve portion where it can sense a signal generated from the patient's brain when the patient wants hand closure. Optional microsensor 2 ($SE_2$) is implanted in a portion of the patient's hand where it can sense a signal corresponding to stimulation/motion of the patient's pinky finger and microsensor 3 ($SE_3$) is implanted and configured to measure a signal corresponding to grip pressure generated when the fingers of the patient's hand are closed. Additionally, an optional microtransponder ($T_1$) is shown which can be used to improve the communication between the SCU 302 and the implanted devices.

Figure 7:
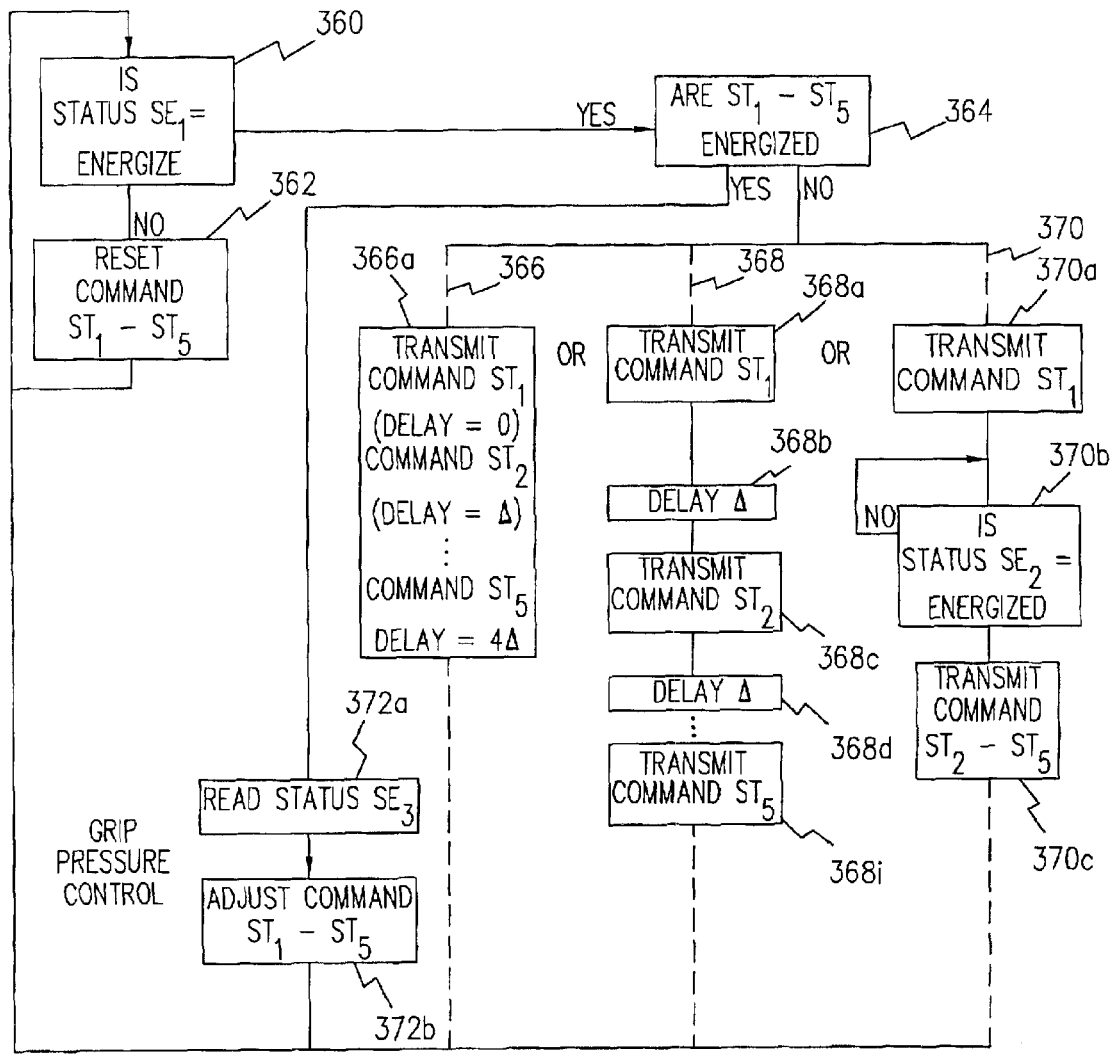
FIG. 7 shows a simplified flow chart of the control of the implanted devices of FIG. 6 by the system control unit.

FIG. 7 shows an exemplary flow chart for the operation of the SCU 302 in association with the implanted devices in the exemplary system of FIG. 6. In block 360, the SCU 302 interrogates microsensor 1 ($SE_1$) to determine if the patient is requesting actuation of his fingers. If not, a command is transmitted in block 362 to all of the stimulators ($ST_1$–$ST_5$) to open the patient's hand, i.e., to de-energize the muscles which close the patient's fingers. If microsensor 1 ($SE_1$) senses a signal to actuate the patient's fingers, the SCU 302 determines in block 364 whether the stimulators $ST_1$–$ST_5$ are currently energized, i.e., generating a sequence of drive/stimulation pulses. If not, the SCU 302 executes instructions to energize the stimulators. In a first optional path 366, each of the stimulators is simultaneously (subject to formatting and transmission delays) commanded to energize in block 366a. However, the command signal given to each one specifies a different start delay time. Accordingly, there is a stagger between the actuation/closing of each finger.

In a second optional path 368, the microstimulators are consecutively energized by a delay $\Delta$. Thus, microstimulator 1 ($ST_1$) is energized in block 368a, a delay is executed within the SCU 302 in block 368b, and so on for all of the microstimulators. Accordingly, paths 366 and 368 perform essentially the same function. However, in path 366, the interdevice timing is performed by the clocks within each implanted device 100 while in path 368, the SCU 302 is responsible for providing the interdevice timing.

In path 370, the SCU 302 actuates a first microstimulator ($ST_1$) in block 370a and waits in block 370b for its corresponding muscle to be actuated, as determined by microsensor 2 ($SE_2$), before actuating the remaining stimulators ($ST_2$–$ST_5$) in block 370c. This implementation could provide more coordinated movement in some situations.

Once the stimulators have been energized, as determined in block 364, closed loop grip pressure control is performed in blocks 372a and 372b by periodically reading the status of microsensor 3 ($SE_3$) and adjusting the commands given to the stimulators ($ST_1$–$ST_5$) accordingly. Consequently, this exemplary system has enabled the patient to regain control of his hand including coordinated motion and grip pressure control of the patient's fingers.

Figures 8A, 8B:
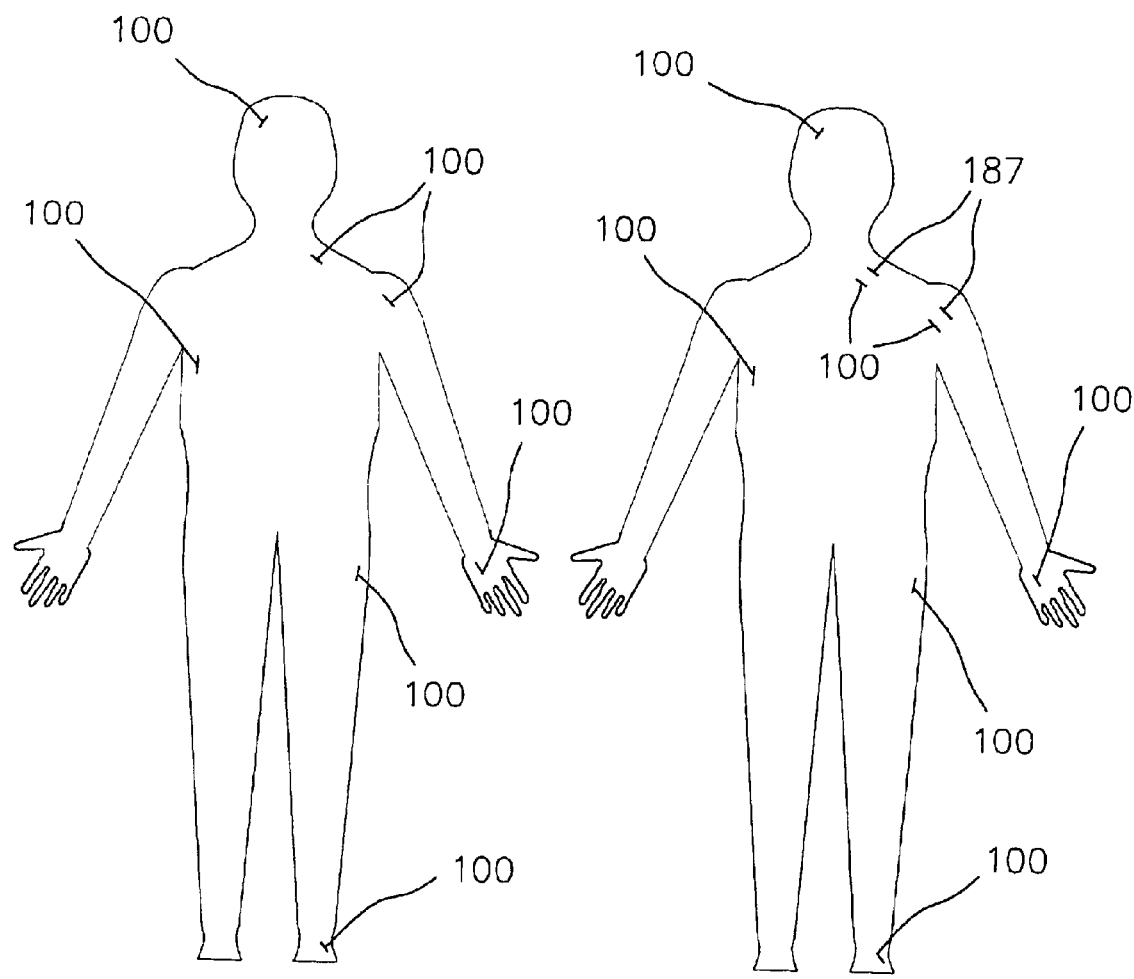
FIGS. 8A and 8B respectively show an exemplary patient having a plurality implanted devices within and the application of a magnetic programmer proximate to one of the implanted devices to alter the programming of the proximate implanted device by sequential applications of magnetic fields having two or more of the following distinct magnetic properties: (1) intensity (including absence or presence), (2) duration, and (3) polarity.
Figure 9:
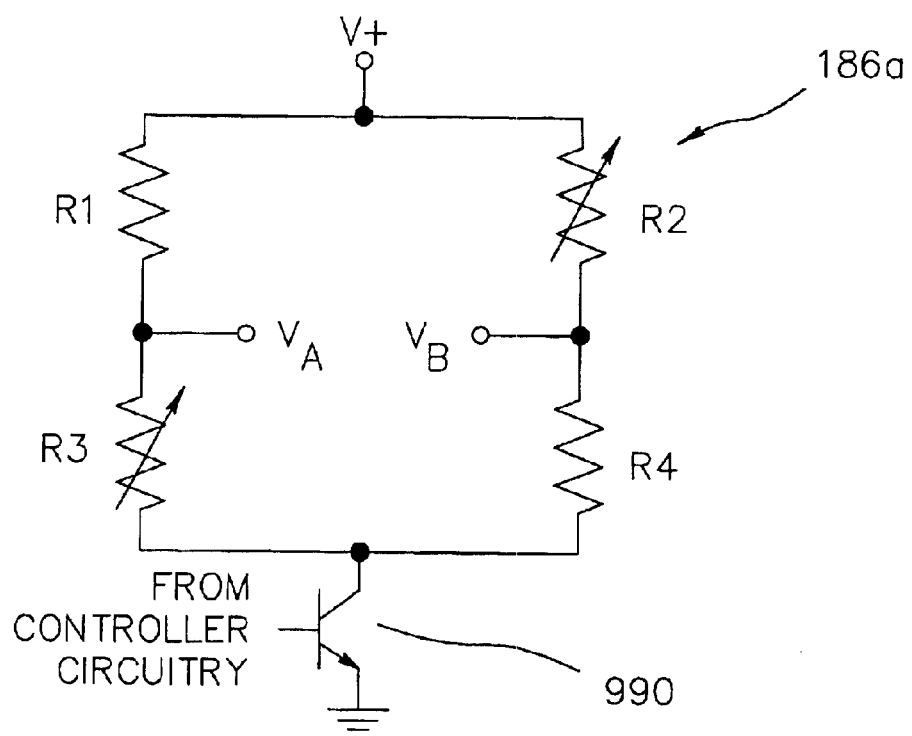
FIG. 9 shows the structure of a conventional magnetoresistive sensor as a bridge circuit wherein such a structure is useful for the programming operation of the present invention when used in an implantable device.

Referring again to FIG. 3A, a magnetic sensor 186 is shown. In the '284 patent, it was shown that such a sensor 186 within each implanted device 100 could be used to disable the operation of an implanted device 100, e.g., to stop or otherwise alter the operation of such devices in an emergency situation, in response to a DC magnetic field, preferably from an externally positioned magnet 187 (see the safety magnet of FIG. 1). Additionally, note FIG. 8A which shows an exemplary patient having a plurality of devices 100 implanted within and FIG. 8B which shows the application of an external magnet 187, i.e., a hand magnetic programmer, proximate to one of the implanted devices to alter the programming, e.g., stimulation pulse properties of the proximate implanted device 100 or system programming, by sequential applications of a magnetic field having two or more of the following distinct magnetic properties: (1) intensity (including absence or presence), (2) duration, and (3) polarity. It is also noted that power to at least some portions of a preferred implantable device may be removed when a magnetic field is sensed and thus the battery life of the overall device may be extended. The magnetic sensor 186 may be implemented using various types of devices. Exemplary of such devices are devices manufactured by Nonvolatile Electronics, Inc. (e.g., their AA, AB, AC, AD, or AG series), Hall effect sensors, magnetoresistive sensors, and subminiature reed switches. Such miniature devices are configurable to be placed within the housing of the SCU 302 and implantable devices 100. While essentially passive magnetic sensors, e.g., reed switches, are possible, the remaining sensor devices may include active circuitry that consumes power during detection of the DC magnetic field. Accordingly, it is preferred that controller circuitry 106 periodically, e.g., one to ten times a second, provides power to the magnetic sensor 186 (see, for example, transistor 990 in FIG. 9 which provides/removes the ground reference for the sensor 186*a*) and then samples the magnetic sensor's output signal 374 (comprised, for example, of a differential output signal $V_B$-$V_A$ in FIG. 9) during that sampling period. This power switching reduces the power consumption related to the sensor 186 while still providing a sufficient sample rate to measure the intensity and sense transitions of the magnetic field.

Figure 10:
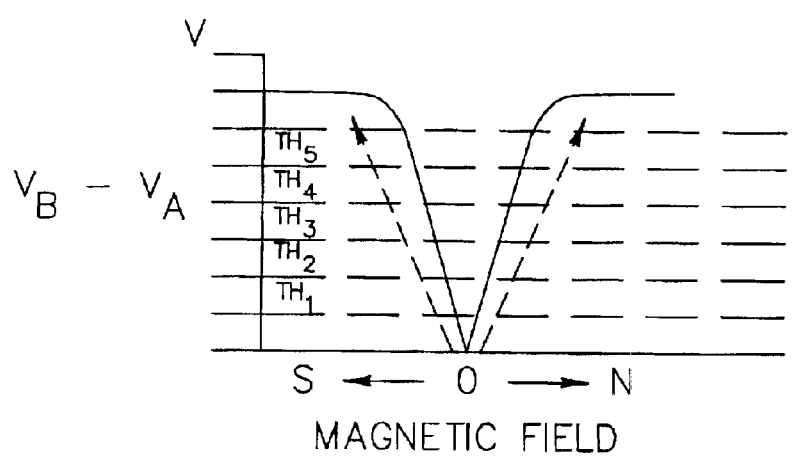
FIG. 10 shows an exemplary response curve showing the differential output voltage of the structure of FIG. 9 in response to the application of a magnetic field wherein the circuit of FIG. 9 may be used to sense the intensity of an applied magnetic field.

A magnetoresistive sensor is especially preferred due to its small size that enables its use within the preferred implantable device 100 while conserving the available internal package volume. An exemplary magnetoresistive sensor 186*a* (see FIG. 9) is typically formed as a bridge circuit from a plurality of magnetoresistive elements (e.g., $R_2$, $R_3$) that are formed in such a manner that the presence of a magnetic field causes their resistance to decrease. Typically, structure is present in such devices that concentrates the magnetic effects to elements $R_2$, $R_3$, while blocking or reducing magnetic effects to elements $R_1$, $R_3$ (which otherwise are magnetoresistive elements and subject to similar effects). The net result is that the differential output voltage ($V_B$-$V_A$) increases in an essentially linear manner following the intensity of the applied magnetic field (see FIG. 10). In a conventional magnetoresistive device, the differential output voltage increases dependent upon the applied magnetic field strength (i.e., dependent upon the size of an external magnet and its distance from the magnetoresistive sensor) but independent of the applied polarity (N or S) of the external magnet. Thus, multiple threshold levels, e.g., $TH_1$-$TH_4$, may be detected (e.g., by controller circuitry 106 or an intermediate analog voltage sensing circuit) as data values or to discriminate the sensor's response to unwanted magnetic fields. For example, an output voltage below $TH_1$ would indicate that a magnetic field is not present, while an output voltage above $TH_4$ would indicate that a magnetic field is greater than that used for programming, e.g., from an MRI device or the like, and should, accordingly, be ignored.

Figure 12:
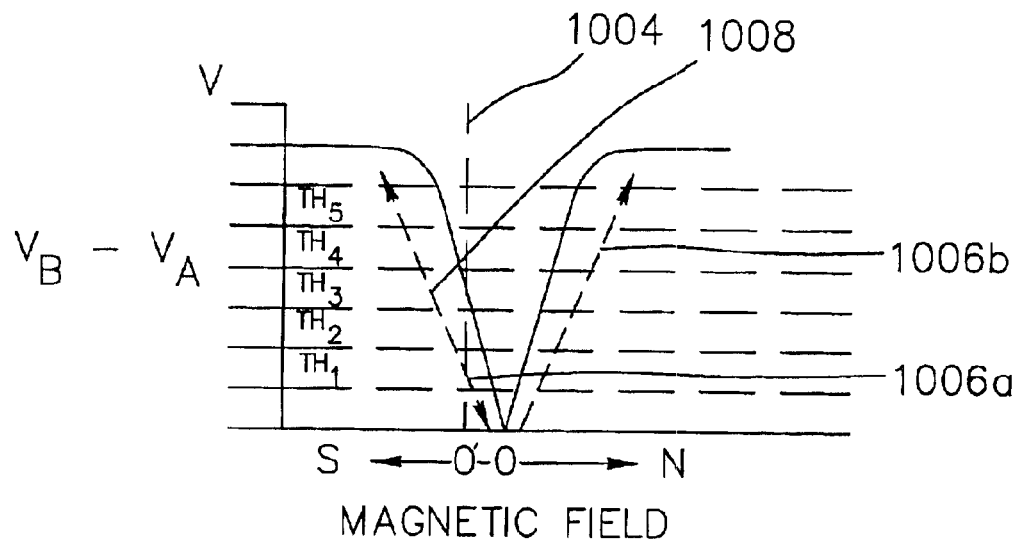
FIG. 12 shows an exemplary response curve showing the differential output voltage of the structure of FIG. 11 in response to the application of a magnetic field wherein the zero point of its response curve has been shifted from that of FIG. 10 and, accordingly, the device of FIG. 11 may be used to sense the intensity and polarity of an applied magnetic field.
Figure 11:
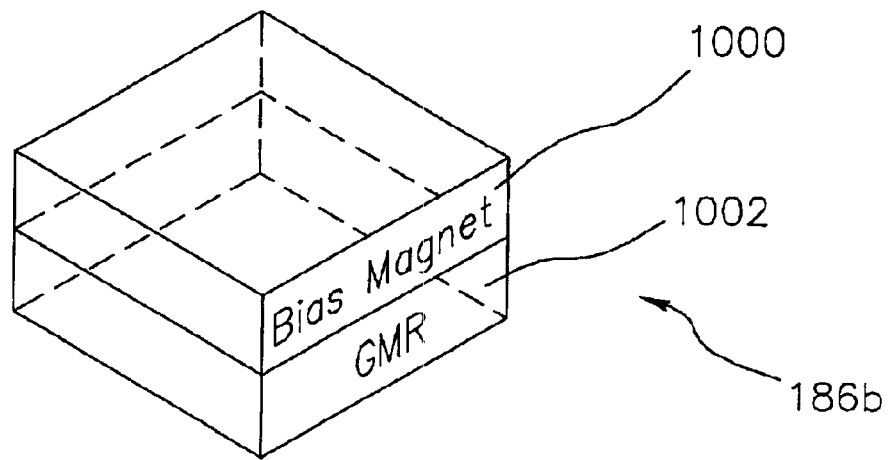
FIG. 11 shows an exemplary structure of a magnetoresistive sensor that has been modified by application of a bias magnet to enable said sensor to additionally detect the polarity of an applied magnetic field.

Alternatively, a bias magnet 1000 may be placed proximate to a magnetoresistive sensor 1002 (also referred to as a Giant MagnetoResistive device or GMR) and thus form a magnetic sensor 186*b* (see FIG. 11) that can additionally detect the polarity of an applied magnetic field. As seen in FIG. 12, the bias magnet 1000 has shifted the zero applied magnetic field point from 0 to 0' (see vertical dashed line 1004) and the differential output voltage at this zero point is no longer a low, e.g., zero, voltage. When a magnetic field is applied of sufficient intensity (and of the correct opposing polarity) to match (and thus cancel) the applied field from the bias magnet 1000, the differential output voltage shifts downward and if the applied magnetic field overcomes the intensity of the bias magnet 1000, the differential output voltage increases again (see dashed differential output voltage curve portions 1006*a* and 1006*b*). By sensing this voltage transition, the controller circuitry 106 can detect the presence of an opposing polarity magnetic field and its intensity according to its final differential output value and its relationship to defined threshold values, e.g., $TH_1$-$TH_4$. Conversely, if a non-opposing magnetic field is applied, the differential output voltage will increase along the same side of the curve (see dotted curve portion 1008).

When an external programmer is available, it typically provides full access to all or most of the programmable features of such implantable devices 100. However, external programmers may be unavailable at certain times or in certain environments due to cost, size, or other constraints. Accordingly, in embodiments of the present invention, an externally provided magnetic field, e.g., from a permanent magnet such as 187, is applied in sequences of controlled polarities, durations, intensities, etc. to provide programming information that may be sensed by the magnetic sensor 186 and used under control of controller circuitry 106 to alter the programming of the implantable device 100. Typical of such programming, is the amplitude, duration, frequency, etc. of stimulation pulses generated by such devices.

In an exemplary embodiment, a magnet (used as a passive hand magnetic programmer 187) is placed close enough to the magnetic sensor 186 in device 100 to control (shut down) the device 100 as well as program it to change programmable parameters such as pulse frequency (rate), pulse amplitude, pulse width and other parameters. The number of parameters and increments are only limited to a reasonable amount of time and the timing skill of the patient. The sensor 186 and its associated controller circuitry 106 is programmed to recognize the presence of one or more of the following magnetic properties: (1) the absence or presence of a magnetic field, (2) the magnetic field's relative strength, (3) the magnetic field's polarity, and/or (3) the length of time the magnetic field is applied. A typical time increment is 2 seconds and this is used in the following programming examples.

Figure 13:
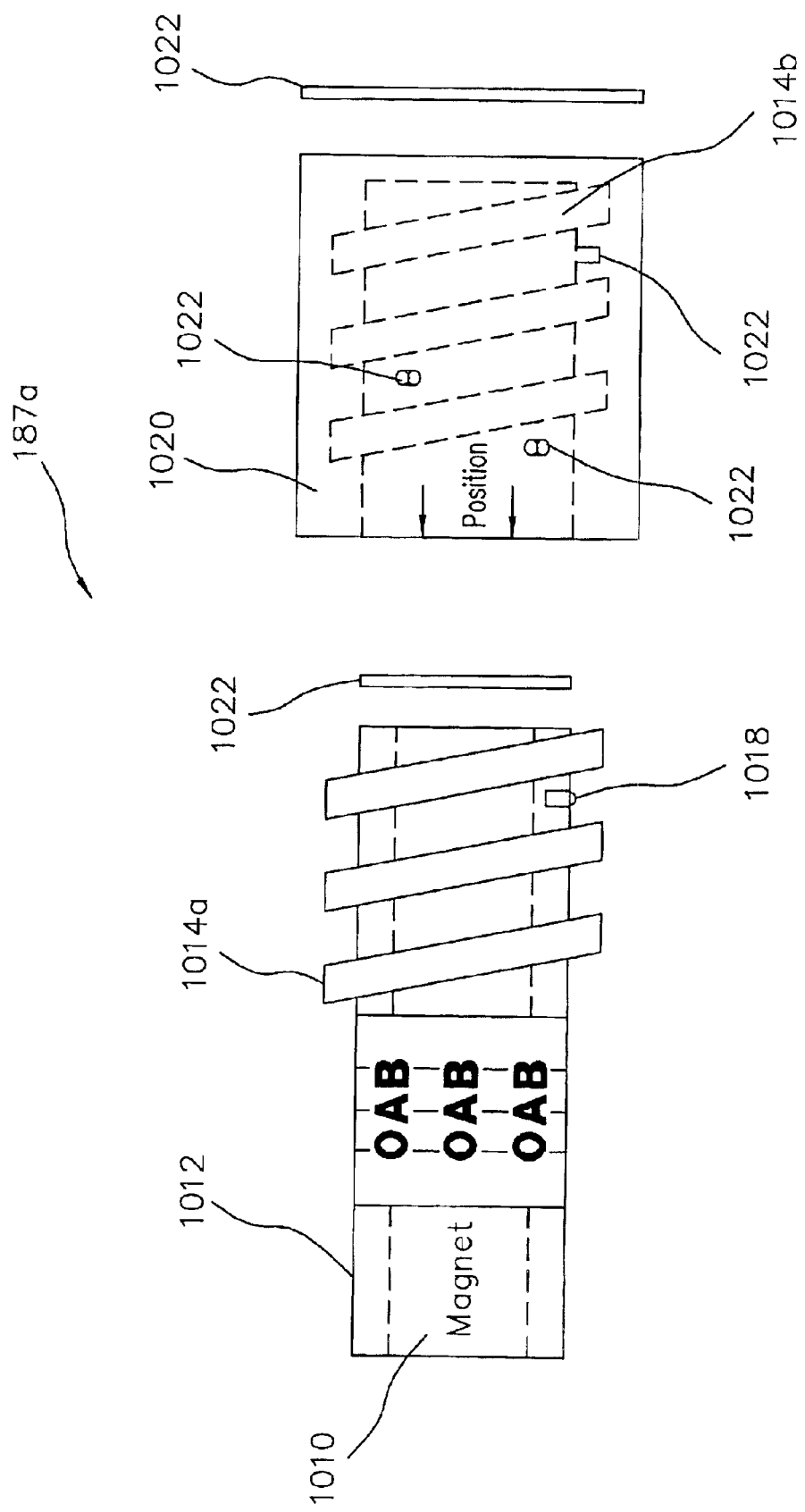
FIG. 13 shows the structure of an exemplary cylindrically shaped passive hand magnetic programmer.

For use as an external passive magnetic programmer, the pole of a magnet 1010 in the passive hand magnetic programmer 187 is of the same polarity as the bias magnet 1000 and positioned slightly further into a holder, (see, e.g., cylindrical tube 1012 in FIG. 13). The positioning of the magnet 1010 in the holder is based on several factors: (1) magnet size and type, especially its strength, (2) the type of field sensor used in the implant, (3) the depth of the living tissue stimulator in the body, and (4) the distance of the magnet 1010 from the skin and, accordingly, the distance from the magnetic sensor 186 within the implantable device 100. Preferably, the system uses the weakest suitable magnet. An exemplary number of magnet field strengths, e.g., three (3), may be achieved using a biased magnetic sensor, e.g., 186*b*, to sense magnetic polarity. These selections may be used in combination with an exemplary number of application times or programming sequences, e.g., three (3), to achieve nine (9) programmable parameters. The use of two magnetic poles doubles the number of codes that can be sensed to eighteen (18) (see Table A). If the poles are alternated in defined sequences, even more combinations may be used. This potential number of programmable parameters far exceeds the requirements for a simple "emergency" hand controller and thus further facilitates the use of the present invention as a programmer.

TABLE A

Available Programming Codes

| Magnetic Field Strength → | A | B | C |
|---|---|---|---|
| Magnet Polarity-N | | | |
| Application Timing ▼ | | | |
| A | 1 | 2 | 3 |
| B | 4 | 5 | 6 |
| C | 7 | 8 | 9 |
| Magnet Polarity-S | | | |
| A | 10 | 11 | 12 |
| B | 13 | 14 | 15 |
| C | 16 | 17 | 18 |

Figure 14:
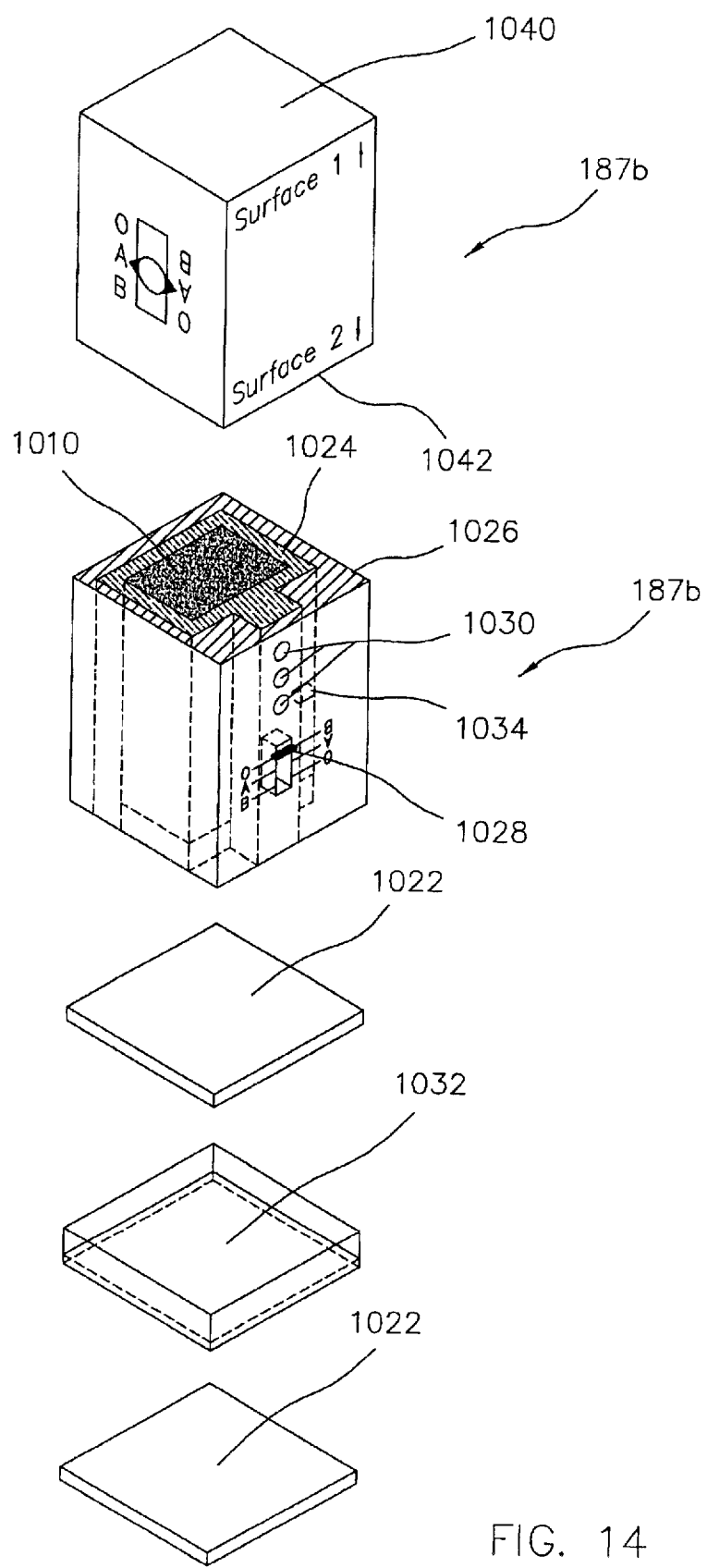
FIG. 14 shows the structure of an exemplary square shaped passive hand magnetic programmer.

Magnets, e.g., comprised of Neodymium-Iron-Boron, NIB, Rare Earth Supermagnets, are easily made in any shape (square, sphere, round, etc.) and may be magnetized with just about any desired pole orientation and number of poles. Accordingly, two exemplary external passive magnetic programmers are shown for a round magnetic programmer 187a and a square magnetic programmer 187b in FIGS. 13 and 14, respectively.

A. Round Magnetic Programmer 187a (see FIG. 13)

A magnet 1010 is contained in a plastic cylindrical tube 1012 of approximately the same inside length and diameter as the magnet 1010 that it holds. The inside dimension of the tube 1012 is configured for the magnet 1010 to slide in with sufficient clearance to hold the magnet securely. Alternatively, an adhesive may be used. The tube wall thickness is configured to contain a thick course thread 1014a that mates with the inside thread 1014b of an end cap 1020. The threads 1014a and 1014b are preferably course enough to provide approximately one quarter inch per turn or approximately four turns per inch. The inside thread 1014b of the end cap 1020 preferably contains a plurality of ball detents (spring and ball) 1022, typically three, that mate with a ball plunger 1018 in the wall of tube 1012. Preferably, the end cap 1020 can be easily turned and "snap" into place to fix the spacing of the outside surface of the end cap 1020 with respect to the magnet 1010 within the tube 1012 and has a wall thickness adequate to contain the ball plunger 1018 to "lock" the cap 1020 in three distinct positions as defined by the locations of the ball detents 1022. The exemplary cylindrical tube 1012 has a longitudinal line and "tic" markings for each of the positions, 0, A, & B for each pole.

Each passive hand magnet programmer 187 is preferably "calibrated" to the specific implant for its distance from the skin. This may done by gluing plastic calibration discs 1022 to the tube 1012 or the end cap 1020 to set the magnet strength to match the implant requirements. Calibration discs 1022 are of a range of thickness to be added by the clinician when the implant is being initially fitted.

B. Square Magnetic Programmer 187b (see FIG. 14)

The square magnetic programmer embodiment 187b operates on essentially the same principle as the round magnetic programmer embodiment 187a, the difference is primarily in the way the magnet 1010 is moved. The magnet 1010 is held in a non-magnetic frame 1024 that slides inside its housing 1026. A lever 1028 with detents 1030 moves the magnet 1010 towards or away from the end caps 1032 and is held in place by a plunger 1034. This design is preferred for use with a unipolar system or for patients with limited grasp for turning the end caps of the cylindrical design.

In a first example which follows, a preferred embodiment of a magnet control system is implemented in device 100 using one level of field strength and independent of magnetic polarity. The action to shut down the implant is the same, independent of polarity in systems that use magnetic polarity to increase the number of programmed parameters. An exemplary polarity and timing sequence is described below.

Figure 15:
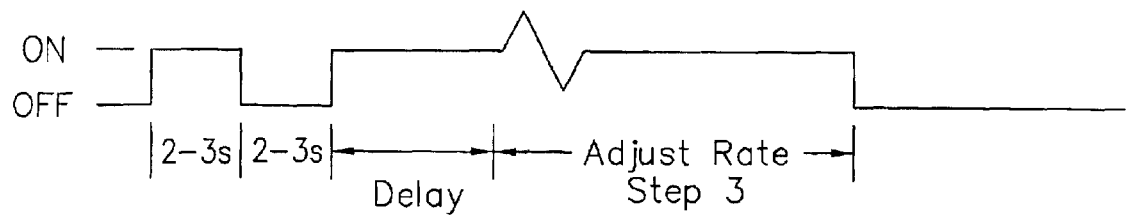
FIG. 15 shows a timing diagram of an exemplary programming sequence using a passive hand magnetic programmer.
Figure 15:
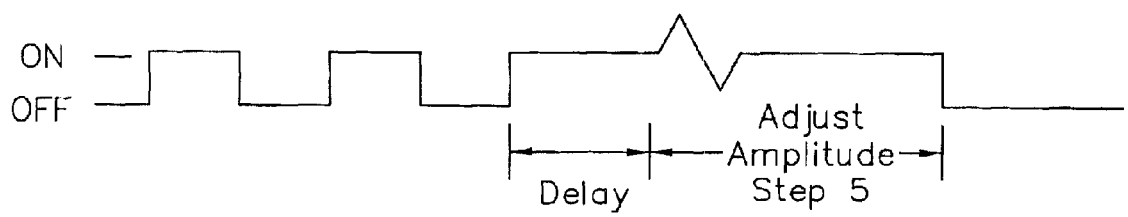
Figure 15:
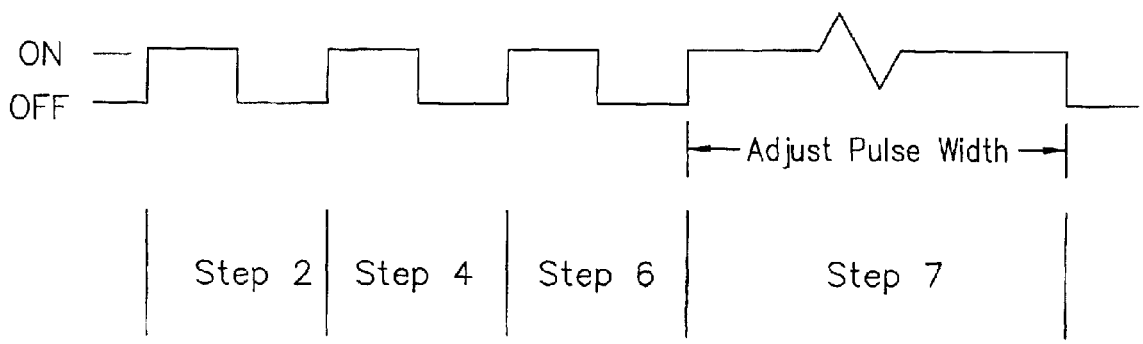

In this first example, implant control is done with hand magnet programmer 187b using a first surface 1040 pressed to the skin and the slider 1028 set to position zero (see the exemplary timing diagram of FIG. 15).

| Step No. | Action | Response |
|---|---|---|
| 1. Shut down | Hand magnetic programmer surface 1040 is placed on the skin and not removed for a time period in excess of the number of the programmable parameters (N) times the programming period, e.g., 2 seconds, that is for a time period >2*N. | Implant is turned off and remains off as long as the magnet 1010 is held close to the skin. |
| 2. Select Mode | Remove the hand magnetic programmer for a reset time period, e.g., 2 to 3 seconds. Hand magnetic programmer surface 1040 is then replaced on the skin for 2 seconds and then removed for 2 to 3 seconds. | Implant 100 responds and sets Pulse Rate mode. |
| 3. Set Parameter | Following step 2, hand magnetic programmer surface 1040 is placed on the skin and held as required (e.g., for a minimum of 3 seconds). The length of time required will depend on the number parameters and the method used to sense the desired parameter. | Implant 100 responds and cycles through pulse rates stepping from one rate to the next as programmed for the stimulation and patient. The magnet 1010 is removed when the desired rate is reached. |
| 4. Select Mode | Following steps 2 and 3, hand magnetic programmer surface 1040 is placed on the skin for 2 seconds and then removed for 2 to 3 seconds. | Implant 100 responds and sets Pulse Amplitude mode. |
| 5. Set Parameter | Following step 4, hand magnetic programmer surface 1040 is placed on the skin and held as required (e.g., for a minimum of 3 seconds. The length of time required will depend on the number parameters and the method used to sense the desired parameter. | Implant 100 responds and cycles through pulse amplitudes stepping from one amplitude to the next as appropriate for the stimulation and patient. The magnet 1010 is removed when the desired amplitude is reached. |

-continued

| Step No. | Action | Response |
| --- | --- | --- |
| 6. Select Mode | Following steps 4 and 5, hand magnetic programmer surface 1040 is placed on the skin for 2 seconds and then removed for 2 to 3 seconds. | Implant 100 responds and sets Pulse Width mode. |
| 7. Set Parameter | Following step 6, hand magnetic programmer surface 1040 is placed on the skin and held as required. The length of time required will depend on the number parameters and the method used to sense the desired parameter. | Implant 100 cycles through pulse widths stepping from one width to the next as appropriate for the stimulation and patient. The magnet 1010 is removed when the desired pulse width is reached. |

If the magnet 1010 is removed for more than 3 seconds following steps 2, 4, or 6, the implantable device 100 reverts to the initial state. If the magnet 1010 is removed for more than 3 seconds following steps 3, 5, or 7, the implant accepts the new programming. This first example can be extended for sufficient steps to allow the implantable device 100 to enter into as many steps as there are programmable parameters and thus a complete system can be formed using a single polarity magnetic programmer 187 and sensor 186.

In a next example, implant control is done with hand magnetic programmer 187*b* using a second surface 1042 pressed to the skin and the slider 1028 set to position zero. These programming modes rely on the ability to distinguish magnetic polarities. Accordingly, a magnetic sensor using the embodiment (or equivalent) described in reference to 186*b* is used within the implantable device 100. This next example is a continuation of the first example that instead incorporates an opposite magnetic polarity as a programming parameter. Otherwise, this second example is essentially the same as the first example.

| Step No. | Action | Response |
| --- | --- | --- |
| 1. Shut down | Hand magnetic programmer surface 1042 is placed on the skin and not removed for a time period in excess of the number of the programmable parameters (N) times the programming period, e.g., 2 seconds, that is for a time period >2*N. | Implantable device 100 is turned off and remains off as long as the magnet 1010 is held close to the skin. |
| 2. Select Mode | Remove the hand magnetic programmer for a reset time period, e.g., 2 to 3 seconds. Hand magnetic programmer surface 1042 is then replaced on the skin for 2 seconds and then removed for 2 to 3 seconds. | Implantable device 100 responds and sets the MRI mode to allow the patient to spend time in a MRI machine. |
| 3. Set Parameter | Following step 2, hand magnetic programmer surface 1042 is placed on the skin and held as required (e.g., for a minimum of 3 seconds). The length of time required will depend on the number parameters and the method used to sense the desired parameter. | Implantable device 100 responds and cycles through MRI schedules stepping from one to the next as required for the time exposed to the MRI. The magnet is removed when the desired schedule is reached. |
| 4. Select Mode | Following steps 2 and 3, hand magnetic programmer surface 1042 is placed on the skin for 2 seconds and then removed for 2 to 3 seconds. | Implantable device 100 responds and sets Pulse Burst mode. |
| 5. Set Parameter | Following step 4, hand magnetic programmer surface 1042 is placed on the skin and held | Implantable device 100 responds and cycles through pulse burst sequences stepping from one to the next |

-continued

| Step No. | Action | Response |
|---|---|---|
| | as required (e.g., for a minimum of 3 seconds). The length of time required will depend on the number parameters and the method used to sense the desired parameter. | as programmed for the stimulation and patient. The magnet 1010 is removed when the desired pulse burst is reached. |
| 6. Select Mode | Following steps 4 and 5, hand magnetic programmer surface 1042 is placed on the skin for 2 seconds and then removed for 2 to 3 seconds. | Implantable device 100 responds and sets Pulse Ramp mode. |
| 7. Set Parameter | Following step 6, hand magnetic programmer surface 1042 is placed on the skin and held as required. The length of time required will depend on the number parameters and the method used to sense the desired parameter. | Implantable device 100 cycles through pulse ramps stepping from one to the next as appropriate for the stimulation and patient. The magnet 1010 is removed when the desired pulse ramp is reached. |

If the magnet 1010 is removed for more than 3 seconds following steps 2, 4, or 6, the implantable device 100 reverts to the initial state. If the magnet 1010 is removed for more than 3 seconds following steps 3, 5, or 7, the implantable device 100 accepts the new programming.

The following example illustrates how the preferred embodiment of a hand magnet programmer/control system is implemented with an implantable device 100 using three levels of field strength and a single magnetic polarity. The timing sequence is described below. The exemplary hand magnet programmer 187b has three positions (see FIG. 14).

| Step No. | Slider Position | Action | Response |
|---|---|---|---|
| 1. Shut down | ANY | Surface of hand magnetic programmer 187 is placed on skin and not removed for a time period in excess of the number of the programmable parameters (N) times the programming period, e.g., 2 seconds, that is for a time period >2*N. | Implantable device 100 is turned off and remains off as long as the magnet 1010 is held close to the skin. |
| 2. Select Mode | 0 | Remove the hand magnetic programmer for a reset time period, e.g., 2 to 3 seconds. Surface of hand magnetic programmer 187 is then replaced on skin for 2 seconds and removed for 2 to 3 seconds. | Implantable device 100 responds and sets Pulse Rate mode. |

-continued

| Step No. | Slider Position | Action | Response |
|---|---|---|---|
| 3. Set Parameter | 0 | Following step 2, the surface of hand magnetic programmer 187 is placed on skin and held as required (e.g., for a minimum of 3 seconds). The length of time required will depend on the number parameters and the method used to sense the desired parameter. | Implantable device 100 responds and cycles through pulse rates stepping from one rate to the next as appropriate for the needed stimulation for the patient. The magnet 1010 is removed when the desired rate is reached. |
| 4. Select Mode | A | Following steps 2 and 3, the surface of hand magnetic programmer 187 is placed on skin for 2 seconds and removed for 2 to 3 seconds. | Implantable device 100 responds and sets Pulse Amplitude mode. |
| 5. Set Parameter | A | Following step 4, the surface of hand magnetic programmer 187 is placed on skin and held as required (e.g., for a minimum of 3 seconds). The length of time required will depend on the number parameters and the method used to sense the desired parameter. | Implantable device 100 responds and cycles through pulse amplitudes stepping from one amplitude to the next as appropriate for the needed stimulation of the patient. The magnet 1010 is removed when the desired amplitude is reached. |
| 6. Select Mode | B | Following steps 4 and 5, the surface of hand magnetic programmer 187 is placed on skin for 2 seconds and removed for 2 to 3 seconds. | Implantable device 100 responds and sets Pulse Width mode. |
| 7. Set Parameter | B | Following step 6, the surface of hand magnetic programmer 187 is placed on skin and held as required. The length of time required will | Implantable device 100 cycles through pulse widths stepping from one width to the next as appropriate for the stimulation and patient. The magnet 1010 is removed when the desired pulse width is reached. |

| Step No. | Slider Position | Action | Response |
|---|---|---|---|
| | | | depend on the number parameters and the method used to sense the desired parameter. |

If the magnet 1010 is removed for more than 3 seconds following steps 2, 4, or 6, the implantable device 100 reverts to the initial state. If the magnet 1010 is removed for more than 3 seconds following steps 3, 5, or 7, the implantable device 100 accepts the new programming.

Combinations of timing and slider positions may be used. Patients with a poor sense of timing, may use position combinations as well. Typical examples include: 0 followed by A, 0 followed by B, A followed by 0, B followed 0, etc. In such programming combinations, the patient may need two hands; one to hold the magnet, the other to move the slider.

Changing the magnet spacing in the magnet holder requires that the magnet sensing circuit 186 be able to recognize various field strengths. In addition, the sensing circuit 186 must also recognize the sequence of field strength changes. As previously discussed, this is accomplished by sampling the field strength, e.g., about 10 times per second, and determining the value compared to previous values. This method is similar to the concept of recognizing, e.g., debouncing, a key press on a keyboard. A key press is valid only if the key is closed in excess of a specific amount of time. The magnetic field strength sensed by sensor 186 must have a consecutive number of equal values (within a range) to recognize a given field strength. This is especially important to prevent slow changing transient fields from accidentally programming the implantable device 100. The time sequence of the programming also reduces susceptibility to accidental programming.

Figure 16A:
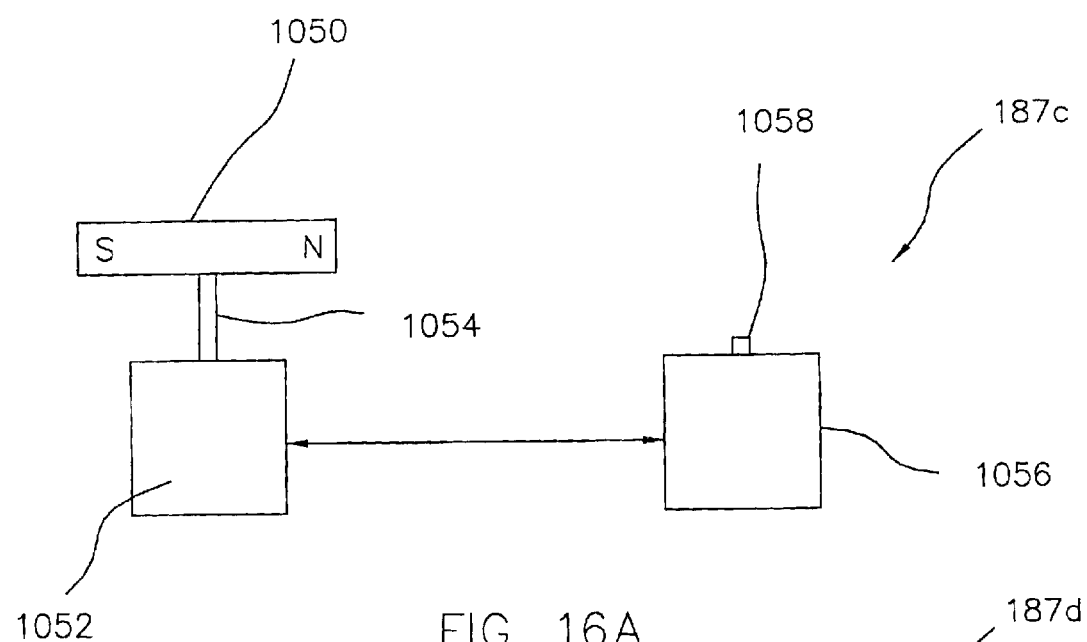
FIGS. 16A and 16B respectively show automatic magnetic programmers that mechanically (or electromechanically) or electrically provide a sequence of magnetic fields that are identifiable to the magnetic sensor within the implantable device.
Figure 16B:
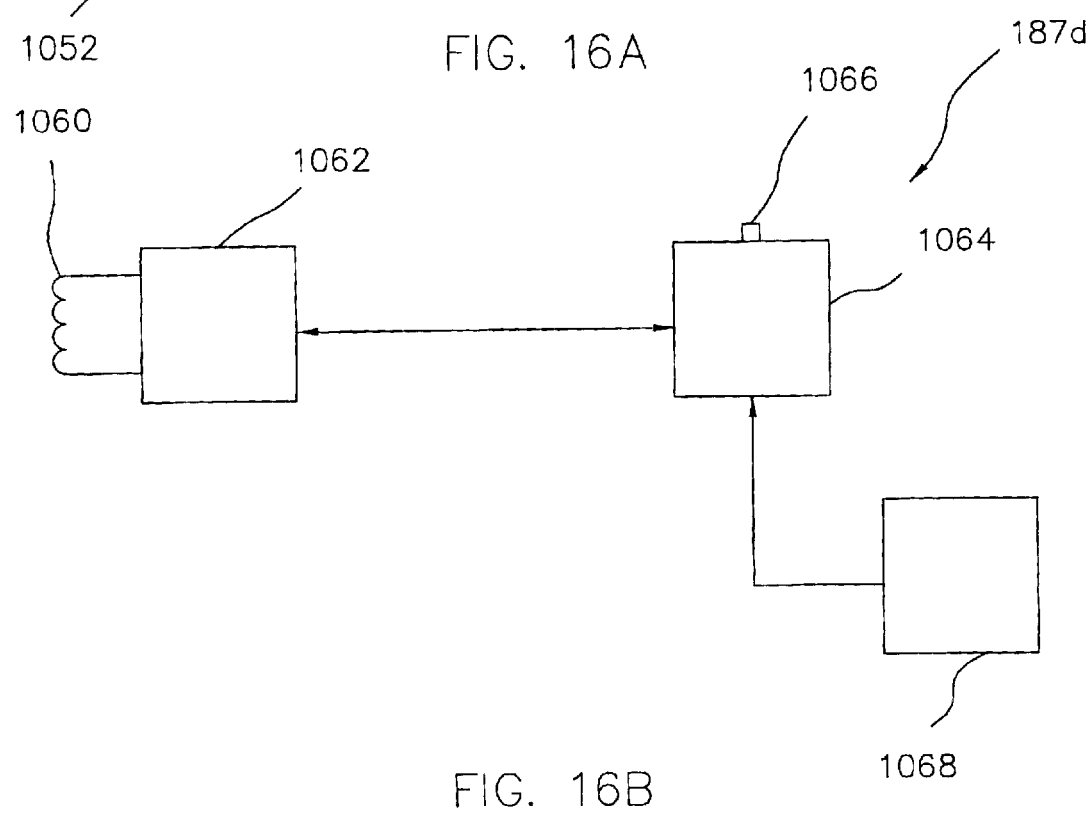

Furthermore, while a purely passive hand programmer 187 is currently preferred, the present invention may also be embodied in a system which is mechanically, e.g., spring driven, to alter the magnetic field in programmable or predefined patterns and thus signal the implantable device 100 which programmable parameter(s) are to be altered. For example, FIG. 16A shows an example of such an embodiment 187c. A magnet 1050 which is coupled to a mechanism 1052, e.g., spring driven, via a shaft 1054. A controller 1056 activates the mechanism 1052 when it receives a command from an operator input 1058. In one variation, controller 1056 may be electrically driven and mechanism 1052 may be electro-mechanical. In a next alternative embodiment 187d shown in FIG. 16B, a coil 1060 may be electrically energized by a driver 1062 under control of a controller 1064 (powered by power source 1068) when activated by a patient input 1066, and thus program one or more programmable parameters of the implantable device 100 automatically.

The use of a magnet is desirable for most applications because it is passive and a magnet may usually be found wherever the patient travels. Magnetic polarity sensing may be used to facilitate programming of multiple parameters or multiple stimulators/sensors 100. Many patients, however, may not be able to use manual timing for programming and will require a more automatic system. In these applications, a light/IR sensor may be used. Such a hand control produces a flash of light that is sensed and recognized by the implantable device 100. This type of system uses batteries to power the active hand control system which provides control based on the number and timing of the flashes.

While the invention herein disclosed has been described by means of specific embodiments and applications thereof, numerous modifications and variations could be made thereto by those skilled in the art without departing from the scope of the invention set forth in the claims. For example, the clinician's programmer 172 could be used to specify a single adjustable parameter (or a limited set of adjustable parameters) and thus the magnetic programmer 187 could be limited to modifying the specified parameter(s) and excluded from modifying the others. Also, the clinician's programmer 172, could be used to restrict the range of adjustment to the one or more adjustable parameters. Alternatively, the presence of the magnetic programmer 187 could be used to determine whether the clinician's programmer 172 would be operative, i.e., its ability to alter the implantable device 100 could be interlocked to require a sensed magnetic field before it would accept programming, thereby increasing the security against program alterations. Other such permutations and combinations thereof can likewise be accomplished with the present invention. It is therefore to be understood that within the scope of the claims, the invention may be practiced otherwise than as specifically described herein.

What is claimed is:

1. A system for programming one or more parameters in an implantable device, wherein said implantable device is configured for stimulating tissue within a patient's body and said implantable device is contained within a sealed elongate housing having an axial dimension of less than 60 mm and a lateral dimension of less than 6 mm, said system comprising:

a sensor within said implantable device sensitive to the presence of an externally applied magnetic field;

a controller within said implantable device coupled to said sensor for monitoring the presence of said externally applied magnetic field and determining a timing sequence for the application and removal of said externally provided magnetic field, wherein said controller is configured to alter at least one programmable parameter of said implantable device in response to detection of an identifiable timing sequence of the application and removal of said externally provided magnetic field;

a handheld programmer configured to be located external to the patient's body and containing a permanent magnet within, wherein the patient can apply and remove a magnetic field according to an identifiable timing sequence by bringing said handheld programmer in proximity and removing it from proximity of the implantable device at one or more locations external to the patient's body; and wherein said handheld programmer additionally comprises a selector for altering the position of said permanent magnet within the programmer to thereby correspondingly alter the strength of said externally applied magnetic field to which the implantable device is exposed when the handheld programmer is positioned in proximity to the implantable device.

2. The system of claim 1 wherein said selector for altering the position of said permanent magnet comprises:
  a first handheld programmer portion having a cylindrical shape, an outer thread, and containing said permanent magnet; and
  a second handheld programmer portion having an inner threaded cavity wherein said inner threaded cavity is formed to receive said outer thread of said first handheld programmer portion and whereby screwing said first handheld portion into said second handheld programmer portion alters the position of said permanent magnet relative to said second handheld programmer portion.

3. The system of claim 2 wherein said selector additionally comprises a ball detent mechanism cooperatively positioned on said first and second handheld programmer portions to fixedly position said permanent magnet relative to said second handheld programmer portion in one of a plurality of predefined positions.

4. The system of claim 1 wherein said selector for altering the position of said permanent magnet comprises:
  a first handheld programmer portion having a square shape and containing said permanent magnet;
  a second handheld programmer portion having an inner cavity wherein said inner cavity is formed to receive said first handheld programmer portion; and
  a detent mechanism for altering the position of said permanent magnet relative to said second handheld programmer portion in one of a plurality of predefined positions.

5. A system for programming one or more parameters in an implantable device, wherein said implantable device is configured for stimulating tissue within a patient's body and said implantable device is contained within a sealed elongate housing having an axial dimension of less than 60 mm and a lateral dimension of less than 6 mm, said system comprising:
  a sensor within said implantable device sensitive to the presence of an externally applied magnetic field;
  a controller within said implantable device coupled to said sensor for monitoring the presence of said externally applied magnetic field and determining a timing sequence for the application and removal of said externally provided magnetic field, wherein said controller is configured to alter at least one programmable parameter of said implantable device in response to detection of an identifiable timing sequence of the application and removal of said externally provided magnetic field;
  a handheld programmer configured to be located external to the patient's body and containing a permanent magnet within, wherein the patient can apply and remove a magnetic field according to an identifiable timing sequence by bringing said handheld programmer in proximity and removing it from proximity of the implantable device at one or more locations external to the patient's body; and wherein
  said handheld programmer has a first surface for presenting a magnetic field of a first polarity and a second surface for presenting a magnetic field of a second polarity, opposite of said first polarity.

6. A system for programming one or more parameters in an implantable device, wherein said implantable device is configured for stimulating tissue within a patient's body and said implantable device is contained within a sealed elongate housing having an axial dimension of less than 60 mm and a lateral dimension of less than 6 mm, said system comprising:
  a sensor within said implantable device sensitive to the presence of an externally applied magnetic field;
  a controller within said implantable device coupled to said sensor for monitoring the presence of said externally applied magnetic field and determining a timing sequence for the application and removal of said externally provided magnetic field, wherein said controller is configured to alter at least one programmable parameter of said implantable device in response to detection of an identifiable timing sequence of the application and removal of said externally provided magnetic field;
  a handheld programmer configured to be located external to the patient's body and containing a permanent magnet within; and
  a mechanism, configured for activation by the patient, within said handheld programmer configured to provide an identifiable timing sequence of the application and removal of a magnetic field.

7. The system of claim 6 wherein said mechanism is spring powered.

8. The system of claim 6 wherein said mechanism is electro-mechanically powered.

9. A system for programming one or more parameters in an implantable device, wherein said implantable device is configured for stimulating tissue within a patient's body and said implantable device is contained within a sealed elongate housing having an axial dimension of less than 60 mm and a lateral dimension of less than 6 mm, said system comprising:
  a sensor within said implantable device sensitive to the presence of an externally applied magnetic field;
  a controller within said implantable device coupled to said sensor for monitoring the presence of said externally applied magnetic field and determining a timing sequence for the application and removal of said externally provided magnetic field, wherein said controller is configured to alter at least one programmable parameter of said implantable device in response to detection of an identifiable timing sequence of the application and removal of said externally provided magnetic field;
  a handheld programmer configured to be located external to the patient's body;
  a coil within said handheld programmer suitable for generating a magnetic field when energized;
  driver circuitry within said handheld programmer for energizing said coil;
  a handheld programmer controller within said handheld programmer for generating a sequence of magnetic fields; and
  a power source for powering said handheld programmer.

10. A system for programming one or more parameters in an implantable device, wherein said implantable device is configured for stimulating tissue within a patient's body and said implantable device is contained within a sealed elongate housing having an axial dimension of less than 60 mm and a lateral dimension of less than 6 mm, said system comprising:
  a sensor within said implantable device sensitive to the presence of an externally applied magnetic field;

a controller within said implantable device coupled to said sensor for monitoring the presence of said externally applied magnetic field and determining a timing sequence for the application and removal of said externally provided magnetic field, wherein said controller is configured to alter at least one programmable parameter of said implantable device in response to detection of an identifiable timing sequence of the application and removal of said externally provided magnetic field; and wherein said sensor dissipates power when sensing a magnetic field and said implantable device additionally comprises circuitry for periodically applying and removing power from said sensor and sampling said sensor during time periods corresponding to when said power is applied.

11. A system for programming one or more parameters in an implantable device, wherein said implantable device is configured for modifying and/or sensing a patient's body parameter, said system comprising:

a sensor within said implantable device sensitive to the presence of an externally applied magnetic field;

a controller within said implantable device coupled to said sensor for monitoring the presence of said externally applied magnetic field and determining a timing sequence for the application and removal of said externally provided magnetic field, wherein said controller is configured to alter at least one programmable parameter of said implantable device in response to detection of an identifiable timing sequence of the application and removal of said externally provided magnetic field;

a handheld programmer configured to be located external to the patient's body and containing a permanent magnet within, wherein the patient can apply and remove a magnetic field according to an identifiable timing sequence by bringing said handheld programmer in proximity and removing it from proximity of the implantable device at one or more locations external to the patient's body; and wherein said handheld programmer additionally comprises a selector for altering the position of said permanent magnet within the programmer to thereby correspondingly alter the strength of said externally applied magnetic field to which the implantable device is exposed when the handheld programmer is position in proximity to the implantable device.

12. The system of claim 11 wherein said selector for altering the position of said permanent magnet comprises:

a first handheld programmer portion having a cylindrical shape, an outer thread, and containing said permanent magnet; and a second handheld programmer portion having an inner threaded cavity wherein said inner threaded cavity is formed to receive said outer thread of said first handheld programmer portion and whereby screwing said first handheld portion into said second handheld programmer portion alters the position of said permanent magnet relative to said second handheld programmer portion.

13. The system of claim 12 wherein said selector additionally comprises a ball detent mechanism cooperatively positioned on said first and second handheld programmer portions to fixedly position said permanent magnet relative to said second handheld programmer portion in one of a plurality of predefined positions.

14. The system of claim 11 wherein said selector for altering the position of said permanent magnet comprises:

a first handheld programmer portion having a square shape and containing said permanent magnet;

a second handheld programmer portion having an inner cavity wherein said inner cavity is formed to receive said first handheld programmer portion; and a detent mechanism for altering the position of said permanent magnet relative to said second handheld programmer portion in one of a plurality of predefined positions.

15. A system for programming one or more parameters in an implantable device, wherein said implantable device is configured for modifying and/or sensing a patient's body parameter, said system comprising:

a sensor within said implantable device sensitive to the presence of an externally applied magnetic field;

a controller within said implantable device coupled to said sensor for monitoring the presence of said externally applied magnetic field and determining a timing sequence for the application and removal of said externally provided magnetic field, wherein said controller is configured to alter at least one programmable parameter of said implantable device in response to detection of an identifiable timing sequence of the application and removal of said externally provided magnetic field;

a handheld programmer configured to be located external to the patient's body and containing a permanent magnet within, wherein the patient can apply and remove a magnetic field according to an identifiable timing sequence by bringing said handheld programmer in proximity and removing it from proximity of the implantable device at one or more locations external to the patient's body; and wherein said handheld programmer has a first surface for presenting a magnetic field of a first polarity and a second surface for presenting a magnetic field of a second polarity, opposite of said first polarity.

16. A system for programming one or more parameters in an implantable device, wherein said implantable device is configured for modifying and/or sensing a Patient's body parameter, said system comprising:

a sensor within said implantable device sensitive to the presence of an externally applied magnetic field;

a controller within said implantable device coupled to said sensor for monitoring the presence of said externally applied magnetic field and determining a timing sequence for the application and removal of said externally provided magnetic field, wherein said controller is configured to alter at least one programmable parameter of said implantable device in response to detection of an identifiable timing sequence of the application and removal of said externally provided magnetic field;

a handheld programmer configured to be located external to the patient's body and containing a permanent magnet within; and a mechanism, configured for activation by the patient, within said handheld programmer configured to provide an identifiable timing sequence of the application and removal of a magnetic field.

17. The system of claim 16 wherein said mechanism is spring powered.

18. The system of claim 16 wherein said mechanism is electro-mechanically powered.

19. A system for programming one or more parameters in an implantable device, wherein said implantable device is configured for modifying and/or sensing a patient's body parameter, said system comprising:
   a sensor within said implantable device sensitive to the presence of an externally applied magnetic field;
   a controller within said implantable device coupled to said sensor for monitoring the presence of said externally applied magnetic field and determining a timing sequence for the application and removal of said externally provided magnetic field, wherein said controller is configured to alter at least one programmable parameter of said implantable device in response to detection of an identifiable timing sequence of the application and removal of said externally provided magnetic field;
   a handheld programmer configured to be located external to the patient's body;
   a coil within said handheld programmer suitable for generating a magnetic field when energized;
   driver circuitry within said handheld programmer for energizing said coil;
   a handheld programmer controller within said handheld programmer for generating a sequence of magnetic fields; and
   a power source for powering said handheld programmer.

20. A system for programming one or more parameters in an implantable device, wherein said implantable device is configured for modifying and/or sensing a patient's body parameter. said system comprising:
   a sensor within said implantable device sensitive to the presence of an externally applied magnetic field;
   a controller within said implantable device coupled to said sensor for monitoring the presence of said externally applied magnetic field and determining a timing sequence for the application and removal of said externally provided magnetic field, wherein said controller is configured to alter at least one programmable parameter of said implantable device in response to detection of an identifiable timing sequence of the application and removal of said externally provided magnetic field; and wherein
   said sensor dissipates power when sensing a magnetic field and said implantable device additionally comprises circuitry for periodically applying and removing power from said sensor and sampling said sensor during time periods corresponding to when said power is applied.

21. A system for programming one or more parameters in an implantable device, wherein said implantable device is configured for modifying and/or sensing a patient's body parameter, said system comprising:
   a sensor within said implantable device sensitive to the presence of an externally applied magnetic field;
   a controller within said implantable device coupled to said sensor for monitoring the presence of said externally applied magnetic field and determining a timing sequence for the application and removal of said externally provided magnetic field, wherein said controller is configured to alter at least one programmable parameter of said implantable device in response to detection of an identifiable timing sequence of the application and removal of said externally provided magnetic field; and wherein
   said implantable device has at least one programmable parameter having an adjustment range prescribed according to settings provided from an external programmer and wherein said controller's ability to alter said at least one programmable parameter is restricted to said prescribed adjustment range.

22. A system for programming one or more parameters in an implantable device, wherein said implantable device is configured for modifying and/or sensing a patient's body parameter, said system comprising:
   a sensor within said implantable device sensitive to the presence of an externally applied magnetic field;
   a controller within said implantable device coupled to said sensor for monitoring the presence of said externally applied magnetic field and determining a timing sequence for the application and removal of said externally provided magnetic field, wherein said controller is configured to alter at least one programmable parameter of said implantable device in response to detection of an identifiable timing sequence of the application and removal of said externally provided magnetic field; and wherein
   said implantable device has a plurality of programmable parameters and wherein a set of said programmable parameters are selected according to settings provided from an external programmer and wherein said controller's ability to alter said programmable parameters is restricted according to said selected set of programmable parameters.

23. A handheld programmer for programming one or more parameters in an implantable device, wherein the implantable device is configured for modifying and/or sensing a body parameter of a patient, said handheld programmer comprising:
   a magnetic field source, wherein said magnetic field source is a permanent magnet;
   a housing for holding said magnetic field source; wherein said housing is configured for application to and removal from a portion of the patient's body and to enabling presenting and removing a magnetic field from said magnetic field source to the implantable device and thereby alter at least one programmable parameter of the implantable device; and
   at least one mechanism for altering the position of said permanent magnet relative to the patient's body and thereby present altered intensities of the corresponding magnetic field to the implantable device and thus alter at least one programmable parameter of the implantable device accordingly.

24. The handheld programmer of claim 23 wherein said at least one mechanism for altering the position of said permanent magnet comprises:
   a first handheld programmer portion having a cylindrical shape, an outer thread, and containing said permanent magnet; and a second handheld programmer portion having an inner threaded cavity wherein said inner thread cavity is formed to receive said outer thread of said first handheld programmer portion and whereby screwing said first handheld portion into said second handheld programmer portion alters the position of said permanent magnet relative to said second handheld programmer portion.

25. The handheld programmer of claim 24 wherein said selector additionally comprises a ball detent mechanism cooperatively positioned on said first and second handheld programmer portions to fixedly position said permanent magnet relative to said second handheld programmer portion in one of a plurality of predefined positions.

26. The handheld programmer of claim 23 wherein said selector for altering the position of said permanent magnet comprises:
- a first handheld programmer portion having a square shape and containing said permanent magnet;
- a second handheld programmer portion having an inner cavity wherein said inner thread cavity is formed to receive said first handheld programmer portion; and
- a detent mechanism for altering the position of said permanent magnet relative to said second handheld programmer portion in one of a plurality of predefined positions.

* * * * *

UNITED STATES PATENT AND TRADEMARK OFFICE
CERTIFICATE OF CORRECTION

PATENT NO. : 6,839,596 B2
DATED : January 4, 2005
INVENTOR(S) : Nelson et al.

It is certified that error appears in the above-identified patent and that said Letters Patent is hereby corrected as shown below:

Title page,
Item [75], Inventors, should read as follows:
-- [75]    Richard J. Nelson, Canyon Country, CA (US); Joseph H. Schulman, Santa Clarita, CA (US); Joseph N. Walker, Canyon Country, CA (US) --

Column 3,
Lines 24-25, to read as follows:
-- having a plurality of implanted devices within the application of a magnetic programmer proximate to one of the --

Column 4,
Line 49, to read as follows:
-- '284 patent, potential implanted devices 100 (see also the --

Column 5,
Line 38, to read as follows:
-- implantable devices 100 operable to sense and/or stimulate a --

Column 12,
Line 3, to read as follows:
-- magnetic field point from 0 to 0' (see vertical dashed line --

Column 16,
Steps No. 4 and 5 of example to read as follows:

| | | |
|---|---|---|
| --4.<br>Select Mode | Following steps 2 and 3, hand magnetic programmer surface 1042 is placed on the skin for 2 seconds and then removed for 2 to 3 seconds. | Implantable device 100 responds and sets Pulse Burst mode. |
| 5.<br>Set Parameter | Following step 4, hand magnetic programmer surface 1042 is placed on the skin and held | Implantable device 100 responds and cycles through Pulse Burst sequences stepping from one to the next-- |

UNITED STATES PATENT AND TRADEMARK OFFICE
CERTIFICATE OF CORRECTION

PATENT NO. : 6,839,596 B2
DATED : January 4, 2005
INVENTOR(S) : Nelson et al.

It is certified that error appears in the above-identified patent and that said Letters Patent is hereby corrected as shown below:

Column 26,
Line 48, to read as follows:
-- configured for modifying and/or sensing a patient's body --

Column 29,
Line 2, to read as follows:
-- threaded cavity wherein said inner threaded cavity is --

Column 30,
Line 7, to read as follows:
-- cavity wherein said inner cavity is formed to --

Signed and Sealed this

Twenty-sixth Day of April, 2005

JON W. DUDAS
*Director of the United States Patent and Trademark Office*